(12) United States Patent
Avdeef et al.

(10) Patent No.: US 8,840,849 B2
(45) Date of Patent: Sep. 23, 2014

(54) PERMEATION DEVICE AND METHOD FOR REDUCING AQUEOUS BOUNDARY LAYER THICKNESSES

(75) Inventors: Alex Avdeef, Reading, MA (US); Per E. Nielsen, Westlake, OH (US)

(73) Assignee: Pion, Inc., Billerica, MA (US)

( * ) Notice: Subject to any disclaimer, the term of this patent is extended or adjusted under 35 U.S.C. 154(b) by 1710 days.

(21) Appl. No.: 11/628,188

(22) PCT Filed: Jun. 1, 2005

(86) PCT No.: PCT/US2005/019196
§ 371 (c)(1),
(2), (4) Date: Jun. 20, 2007

(87) PCT Pub. No.: WO2005/118141
PCT Pub. Date: Dec. 15, 2005

(65) Prior Publication Data
US 2007/0251336 A1    Nov. 1, 2007

Related U.S. Application Data

(60) Provisional application No. 60/575,883, filed on Jun. 1, 2004.

(51) Int. Cl.
| | | |
|---|---|---|
| *G01N 15/08* | (2006.01) | |
| *G01N 15/00* | (2006.01) | |
| *B01F 13/10* | (2006.01) | |
| *B01F 13/08* | (2006.01) | |
| *C12M 1/12* | (2006.01) | |
| *B01L 3/00* | (2006.01) | |
| *B01D 65/08* | (2006.01) | |

(52) U.S. Cl.
CPC ....... *B01F 13/1013* (2013.01); *B01L 2200/143* (2013.01); *B01F 13/1022* (2013.01); *B01F 13/0818* (2013.01); *B01L 2300/0829* (2013.01); *C12M 25/04* (2013.01); *B01L 2300/0681* (2013.01); *B01L 2300/0609* (2013.01); *B01L 3/50255* (2013.01); *B01L 2200/025* (2013.01); *B01D 2321/2041* (2013.01); *B01D 65/08* (2013.01)
USPC ............................................ 422/500; 422/50

(58) Field of Classification Search
CPC ............................... G01N 15/08; G01N 15/00
USPC ............................................ 422/101, 500, 50
See application file for complete search history.

(56) References Cited

U.S. PATENT DOCUMENTS

| | | | | |
|---|---|---|---|---|
| 4,962,044 A | | 10/1990 | Knesel, Jr. et al. | ........... 436/177 |
| 5,215,920 A | * | 6/1993 | Lyman et al. | ............. 435/297.5 |

(Continued)

FOREIGN PATENT DOCUMENTS

| | | |
|---|---|---|
| JP | 56 091801 | 7/1981 |
| JP | 60 166014 | 8/1985 |

(Continued)

OTHER PUBLICATIONS

Avdeef, Al. "Absorption and Drug Development: Solubility, Permeability, and Charge State." Wiley-Interscience, John Wiley & Sons, Inc.; Hoboken, N.J. Table of Contents & Chapter 7; pp. 116-246, Publication Date: Jul. 2003.*

*Primary Examiner* — Christine T Mui
(74) *Attorney, Agent, or Firm* — Rajesh Vallabh; Foley Hoag LLP

(57) ABSTRACT

The invention provides a permeation device (2) comprising a receiving vessel (6) having an aperture adapted for receiving an insert well (4). Both the vessel (6) and well (4) are used as either donor or acceptor compartments for permeability assays. The vessel (6) or well (4) comprises a porous suppor (8)t, which may comprise biological or biomimetic materials, adapted for a molecular entity to permeate therethrough. In one embodiment, a stirring member (24) disposed in the vessel (6) can provide solution agitation to reduce aqueous boundary layer thickness adjacent to the support (8). Boundary layer thicknesses can be reduced by a device (2) of the invention to less than about 15 um such that a molecular entity permeating the support closely approximates in vivo absorption and transport conditions.

50 Claims, 15 Drawing Sheets

(56) References Cited

U.S. PATENT DOCUMENTS

| | | |
|---|---|---|
| 5,900,142 A | 5/1999 | Maloney et al. |
| 6,126,904 A | 10/2000 | Zuellig et al. ............... 422/130 |
| 6,176,609 B1 * | 1/2001 | Cleveland et al. ........... 366/273 |
| 6,368,865 B1 | 4/2002 | Dahl et al. .................... 436/37 |
| 6,410,332 B1 | 6/2002 | Desrosiers et al. ............ 436/37 |

FOREIGN PATENT DOCUMENTS

| | | | | |
|---|---|---|---|---|
| WO | WO 97/49796 | 12/1997 | | |
| WO | WO 03/049841 | 6/2003 | | |
| WO | WO 03065037 A2 * | 8/2003 | ............. | G01N 33/50 |
| WO | WO 2005095950 A1 * | 10/2005 | ............. | G01N 33/15 |

* cited by examiner

PERMEATION DEVICE AND METHOD FOR REDUCING AQUEOUS BOUNDARY LAYER THICKNESSES

CROSS REFERENCE TO RELATED APPLICATIONS

This application claims the priority of U.S. Provisional Application No. 60/575,883 filed Jun. 1, 2004 and entitled, METHOD AND MINIATURIZED DEVICE TO REDUCE THE AQUEOUS BOUNDARY LAYER THICKNESS, which is hereby incorporated by reference herein.

BACKGROUND OF THE INVENTION

Commonly, drug absorption and transport across the blood brain barrier (BBB) or gastrointestinal tract (GIT) is studied via in vitro permeability assays. These assays are typically performed in an apparatus featuring solution filled donor and acceptor compartments separated by a porous support such as a microporous material or structure. A molecular entity such as a drug of interest permeates from the donor compartment into the acceptor compartment through the porous support of the apparatus. For example, to model GIT drug absorption and transport, monolayers of living cells are grown on the porous support to form a lipid membrane permeation barrier. These monolayers often can include Caco-2 type cells. Alternatively, a lipid membrane permeation barrier can be formed by depositing biomimetic materials on or into the porous support for an assay that is often referred to as a parallel artificial membrane permeability assay (PAMPA).

The donor and acceptor compartments of the apparatus are usually incorporated into microtitre plates of various formats to conduct numerous assays simultaneously. The shortcoming with the compartments is that their small volume causes thick aqueous boundary layers of stagnant solution adjacent to the porous support comprising, for example, biological or biomimetic materials. A thick boundary layer along the upper or lower surface of the support can introduce significant errors to permeation measurements. For example, a molecular entity will be physically impeded from passing through the porous support, which comprises a biological or biomimetic material to form a permeation barrier, from the donor to acceptor compartment.

With a conventional PAMPA, the total thickness of the aqueous boundary layers adjacent to the upper and lower surface of the porous support is from about 1,500 to 4,000 microns ($\mu$m). Measurements of, for example, a drug through a permeation barrier in such an assay can be appreciably biased by resistance due to the boundary layers. Indeed, drug studies are replete with lipophilic compounds that have reported permeability values that merely represent that of boundary layers characteristic to a given acceptor or donor compartment.

In vivo GIT boundary layers are usually considered to be from about 30 to 100 $\mu$m thick. Moreover, BBB boundary layers are presumed to be less than 1 $\mu$m. With a standard Caco-2 type cell assay or PAMPA, the total thickness of the aqueous boundary layers adjacent to the porous support is commonly more than 1,500 $\mu$m thick such that the layers tend to become a limiting factor when measuring the permeability of lipophilic compounds. For such assays, it is well established that solution agitation can diminish aqueous boundary layer thickness. A common approach to achieve agitation of solution in the donor and acceptor compartments is to place the compartments on a vibrational body such as an orbital or linear plate shaker. Other approaches for reducing aqueous boundary layer thicknesses include using a chemical sink in the acceptor compartment or to induce a pH gradient across the porous support comprising, for example, biological or biomimetic materials.

These approaches are still unable to reduce boundary layer thicknesses below 300 to 500 $\mu$m, which is necessary to closely model biological conditions, for example, for drug absorption and transport. Moreover, such approaches become even less attractive for donor and acceptor compartments incorporated into microtitre plates. For example, a standard 96 compartment microtitre plate exhibits a high degree of anisotropy across the plate with compartments along its edges being more effectively agitated than those near the center. This sort of anisotropy is even more pronounced in higher density plates such as those with 384 or 1536 compartments.

In view of the interest in using high density microtitre plates to conduct numerous permeation assays simultaneously, minimizing aqueous boundary layer thicknesses is increasingly difficult as smaller donor and acceptor compartments require more vigorous agitation to only marginally reduce boundary layer thickness. Such a shortcoming as well as those mentioned above demonstrate the need to have a convenient means by which to reduce aqueous boundary layer thicknesses in permeation assays. The means should also be adaptable to easily modify a standard Caco-2 type cell assay or PAMPA for in vitro studies of drug absorption and transport.

SUMMARY OF THE INVENTION

The present invention provides a permeation device comprising a receiving vessel having an aperture. The aperture of the vessel is adapted to receive an insert well. Both the receiving vessel and insert well can comprise either the donor or acceptor compartment for a permeability assay. In addition, the insert well comprises a porous support, for example, disposed, attached or formed in a lower section of the well. Alternatively, the support may be, for example, disposed, attached or formed in an upper section of the receiving vessel. The porous support can, for example, comprise biological, biomimetic or both materials. The porous support is adapted for a molecular entity to permeate therethrough as the entity passes from the donor into the acceptor compartment. For example, an entity in solution in the donor compartment permeates from solution, through the support and into solution in the acceptor compartment.

In one embodiment, a stirring member is disposed in the receiving vessel. The stirring member is operable to agitate a solution in, for example, the receiving vessel, insert well or a combination thereof. Solution agitation can reduce the thickness of the boundary layers adjacent to the upper, lower or both surfaces of the porous support. Generally, agitating a solution in the insert well or receiving vessel reduces the thickness of the boundary layer adjacent to, for example, the upper or lower surface, respectively, of the porous support. For example, the boundary layers comprise a portion of solution, which is substantially stagnant. The thickness of the boundary layers can, for example, be reduced such that a molecular entity can permeate the support, which comprises, for example, biological or biomimetic materials, in close approximation to in vivo absorption and transport conditions.

A device of the invention is well suited for a Caco-2 type cell assay or PAMPA. For a Caco-2 type cell assay, the cells are, for example, grown on the porous support. For a PAMPA, a variety of biomimetic materials can be, for example, deposited or assembled on the support or into its pores. A porous support for a device of the invention can also comprise biological or biomimetic materials disposed or grown on the support or in its pores. The aqueous boundary layer thicknesses that are achievable using a device of the invention can be as thin as, for example, 15 µm. The extent of agitation caused by a stirring member disposed in the donor, acceptor or both compartments can also be controlled to adjustably change a boundary layer thickness. By changing the boundary layer thicknesses, a device of the invention can model in vivo absorption and transport across, for example, the GIT. For example, the invention contemplates a controller device or assembly for a stirring member that is calibrated to produce boundary layer thicknesses from, for example, about 500 to 15 µm.

A stirring member for a device of the invention can be composed of any suitable material(s). The member can be inert such that it does not interfere with the assay. For example, a stirring member can be a magnetized or magnetizeable coated metal in which the coating is an inert polymer. A member can also be an inert metal such as stainless steel. A magnetized or magnetizeable member can be moved by, for example, a magnet. Alternatively, a member can be a glass or inert plastic bead that is moved using a vibrational body such as an orbital or linear plate shaker.

In another embodiment, a second stirring member is disposed in the insert well. The second member can also be comprised of such materials as described above. For example, the second stirring member can be inert and moved by a magnet or vibrational body. A device of the invention can also employ both a magnet and vibration body for solution agitation. In one embodiment, a stirring member can also comprise a molecular entity. The invention also contemplates using a plurality of stirring members in either the receiving vessel, insert well or a combination thereof.

A stirring member can be retained in place in an insert well or receiving vessel so as to not contact biological or biomimetic materials therein. A member can also be held in place so as to not contact the porous support. Any suitable means may be used to retain a stirring member for a device of the invention. For example, a member can be retained by constrictions disposed about the interior of the well or vessel or a strainer positioned therein. Alternatively, a retaining member or structure such as, for example, an inert grid associated with the well or vessel can be used to hold the stirring member in place.

In one embodiment, a donor and acceptor plate can comprise a plurality of either insert wells or receiving vessels. Preferably, the plates are standard format microtitre plates. For example, such plates can include 6, 12, 24, 48, 96, 384 or 1536 wells or vessels. These plates are typically composed of inert and non-magnetic materials such as polycarbonate or any other thermoplastic. An insert well or receiving vessel can also be composed of such inert and non-magnetic materials. A donor or acceptor plate of the invention can also be adapted to be easily manipulated by robotic equipment as is understood within the art. The invention also contemplates assays using a plurality of stackable donor and acceptor plates or a plurality of receiving vessels and insert wells, which can also be stacked.

Another embodiment of the invention comprises biological or biomimetic materials disposed on an upper and lower surface of the porous support. For example, cells of the same type can be grown on the upper and lower surface of the porous support. Similarly, cells of a different type can be grown on the upper and lower surface of the support, respectively. Such an arrangement of biological materials is often used in what is referred to as a co-culture assay. A co-culture assay can also be performed by having a first type of biological material disposed or grown on the porous support and a second type of biological material disposed or grown in the insert well or receiving vessel. For a co-culture assay, it can be particularly important to have a means by which to prevent these materials from being contacted by a stirring member, which could potentially damage the materials.

In another embodiment, a probe is disposed in a receiving vessel. The probe can be based on a variety of principles such as, without limitation, thermal sensing, ion selective electrode technology, spectroscopic methods or a combination thereof. Preferably, the probe is used when the stirring member comprises a molecular entity. For example, the entity can be covered by a biological or biomimetic material disposed about the member such that as the member is moved, the molecular entity permeates therethrough and into the receiving vessel. The permeation can be monitored by the probe.

The present invention also provides a method for reducing boundary layer thicknesses. The method comprises providing one or more permeation devices of the invention. A stirring member(s) for the device is then moved to agitate a solution that preferably contains a molecular entity. The agitation of the solution can reduce the thickness of the boundary layers adjacent to the upper, lower or both surfaces of the porous support, which may include biological or biomimetic materials disposed thereon or therein. For example, boundary layer thicknesses are reduced by reducing the portion of solution that is substantially stagnant and adjacent to the porous support.

A reduction in boundary layer thicknesses can allow permeation of a molecular entity through the support, which comprises biological or biomimetic materials, to closely approximate in vivo absorption and transport conditions. The method also contemplates controlling the extent of agitation due to a stirring member(s) so as to adjustably change the boundary layer thicknesses adjacent to the upper, lower or both surfaces of the porous support. A method of the invention can also be carried out with a plurality of vessels or wells incorporated into donor or acceptor plates as described above.

DESCRIPTION OF THE DRAWINGS

Other features and advantages of the present invention will be apparent from the detailed description of the invention that follows herein, taken in conjunction with the accompanying drawings of which.

DETAILED DESCRIPTION OF THE INVENTION

The present invention provides a permeation device comprising a receiving vessel having an aperture adapted for receiving an insert well. Both the receiving vessel and insert well can comprise either the donor or acceptor compartment for a permeability assay. The insert well includes a porous support, for example, disposed, attached or formed in a lower section of the well. Alternatively, the support may be, for example, disposed, attached or formed in an upper section of the receiving vessel. A molecular entity in solution in a donor compartment can permeate the porous support and pass into solution in an acceptor compartment. Preferably, the porous support comprises biological, biomimetic materials or a combination thereof such as, for example, a living cell membrane layer or a non-living lipid layer.

In one embodiment, a solution is agitated by a stirring member disposed in the receiving vessel. By agitating the solution, the aqueous boundary layers adjacent to the upper, lower or both surfaces of the porous support, which comprises, for example, biological or biomimetic materials, can be reduced such that permeation of a molecular entity therethrough closely models in vivo absorption and transport. Generally, agitating a solution in the insert well or receiving vessel reduces the thickness of the boundary layer adjacent to, for example, the upper or lower surface, respectively, of the porous support. For example, boundary layer thicknesses adjacent to the support can be reduced to approximate absorption and transport conditions in the GIT. Boundary layer thicknesses are reduced by, for example, reducing the portion of solution that is substantially stagnant and adjacent to the porous support.

A device of the invention can reduce the total thickness of the aqueous boundary layers to less than, for example, 15 µm. The extent of agitation due to a stirring member can also be controlled to adjustably change boundary layer thicknesses. By adjustably changing boundary layer thicknesses, a device of the invention can model in vivo absorption and transport across, for example, the GIT. For example, the invention contemplates a controller device or assembly for the stirring member that is calibrated to produce boundary layer thicknesses from, for example, about 500 to 15 µm. A device of the invention can also be used for a conventional Caco-2 type cell assay or PAMPA in which the biological or biomimetic materials are, for example, comprised by the porous support.

Figure 1:
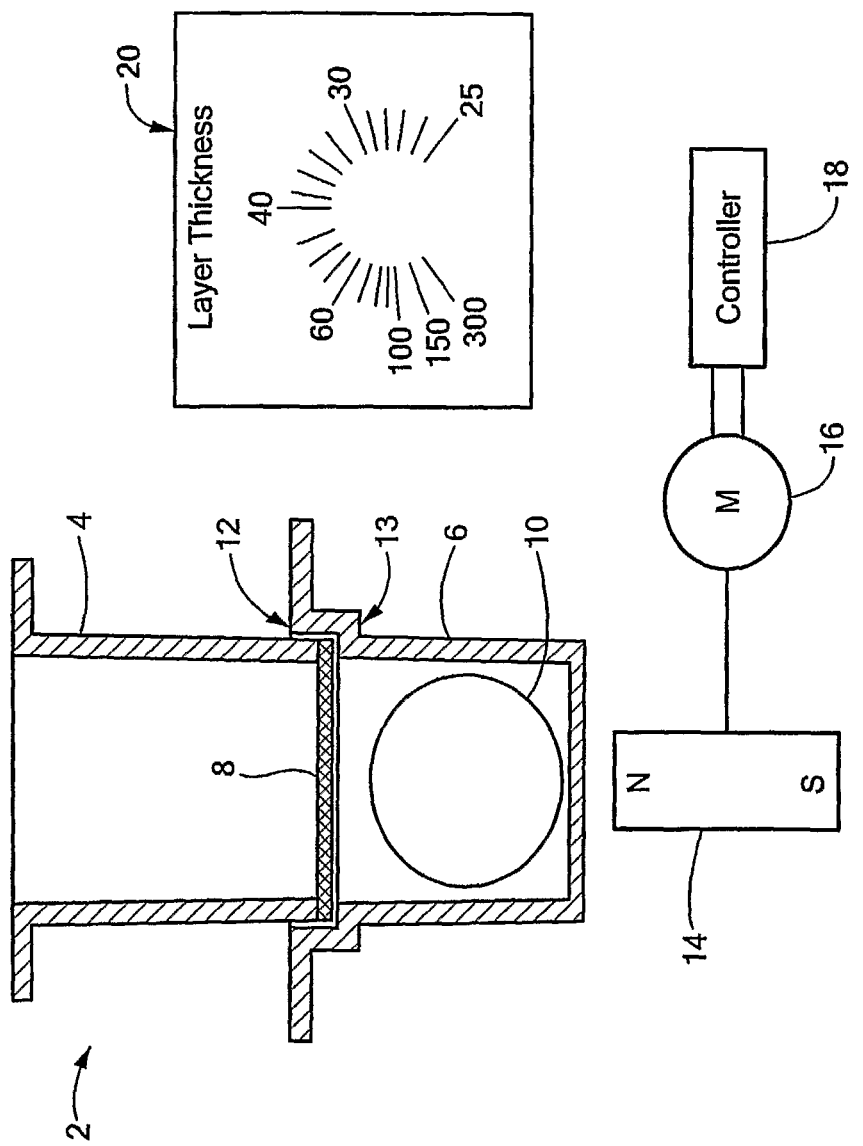
FIG. 1 is a partial representation of a device of the invention having a stirring member disposed in a receiving vessel.

FIG. 1 shows a partial representation of a device of the invention. As shown, a device 2 comprises a receiving vessel 6 having an aperture. An insert well 4 is disposed in the vessel 6 through the aperture. A lower section of the well 4 comprises a porous support 8. The porous support 8 can be, for example, disposed, attached or formed in the lower section of the insert well 4. The support can also be adapted to receive a biological or biomimetic material disposed or grown on its upper or lower surface. Such materials can also be disposed or grown on both the upper and lower surfaces of the support 8. Similarly, these materials can be disposed or grown in the pores of the support. For example, a non-living, biomimetic lipid-based membrane can be assembled on the support or in its pores.

The receiving vessel 6 can include a stirring member 10. The member 10 can be inert such that it does not interfere with an assay. For example, a stirring member can be a magnetized or magnetizeable coated metal in which the coating is an inert polymer. A member can also be an inert metal such as stainless steel. A magnetized or magnetizeable member can be moved by, for example, a magnet. The magnet can, for example, be fixed with respect to the receiving vessel such that the magnet is positioned substantially beneath the vessel.

FIG. 1 shows the member 10 as a thin ferromagnetic or paramagnetic disk attracted to a permanent magnet 14 below the bottom of the vessel 6 so as to keep the magnet away from the support 8. The magnet is rotated by a motor 16, which can be controlled using a controller device 18. Alternatively, a stirring member can be a glass or inert plastic bead that is moved using a vibrational body such as an orbital or linear plate shaker. The vibrational body can also be, for example, fixed with respect to the receiving vessel such that the body is positioned substantially beneath the vessel.

In FIG. 1, as the motor 16 turns, the stirring member 10 also turns or moves. When solution(s) is added to the well 4 and vessel 6 of the permeation device 2, the thickness of the aqueous boundary layer adjacent to, for example, the upper, lower or both surfaces of the porous support 8 can be controlled by the speed of the motor. In general, a stirring member that is disposed in a receiving vessel predominately reduces the aqueous boundary layer along the lower surface of a porous support disposed between the vessel and an insert well. Similarly, a stirring member that is disposed in an insert well predominately reduces the aqueous boundary layer along the upper surface of the porous support disposed between a receiving vessel and the well. For example, boundary layer thicknesses are reduced by reducing the portion of solution that is substantially stagnant and adjacent to the porous support.

As described above, a boundary layer comprises a portion of solution that is substantially stagnant. Solutions in both the insert well 4 or receiving vessel 6 comprise such a substantially stagnant portion adjacent to the upper and lower surface, respectively, of the porous support 8. It is also contemplated that the speed of the motor 16 for a permeation device 2 can be calibrated in terms of the thickness of the aqueous boundary layers adjacent to the upper, lower or both surfaces of the porous support.

For example, FIG. 1 shows a scaled potentiometer 20, which is calibrated to adjustably change the boundary layer thickness adjacent to the lower surface of the porous support via the motor 16 and controller device 18. Such motor control and calibration can readily be performed using conventional laboratory techniques that may include computer software and hardware. A motor, controller device and potentiometer are also exemplary means by which to adjustably change boundary layer thicknesses, although the invention contemplates that any other suitable means can also be used.

In one embodiment, the device 2 comprises a receiving vessel 6 that features an upper portion 12 and flange 13, which are intended to accommodate and support the insert well 4. The upper portion can have a diameter larger than that of the main body portion of the receiving vessel 6. The insert well 4 can alternatively be supported by any suitable means such as a supporting element or member positioned substantially along the exterior or interior of the vessel 6, which may obviate the need for an upper portion 12 having a diameter larger than that of the main body portion of the vessel.

The receiving vessel 6 and insert well 4 may be formed from any suitable materials. For example, inert or non-magnetic materials such as polycarbonate or any other thermoplastic can be used for the vessel and well. The porous support 8 for a device of the invention can also be made from any suitable material such as, for example, polyvinylidene fluoride (PVDF), polyethylene terephtaleate or polycarbonate. In addition, the support preferably has an exemplary thickness from about 10 to 200 µm and an exemplary porosity from about 5 to 80 percent. The support 8 can be disposed, attached or formed in the insert well 4 by any suitable bonding technique known to produce a secure and leak-free attachment. Exemplary techniques include solvent bonding, heat-sealing, insert molding and ultrasonic welding.

Figure 2:
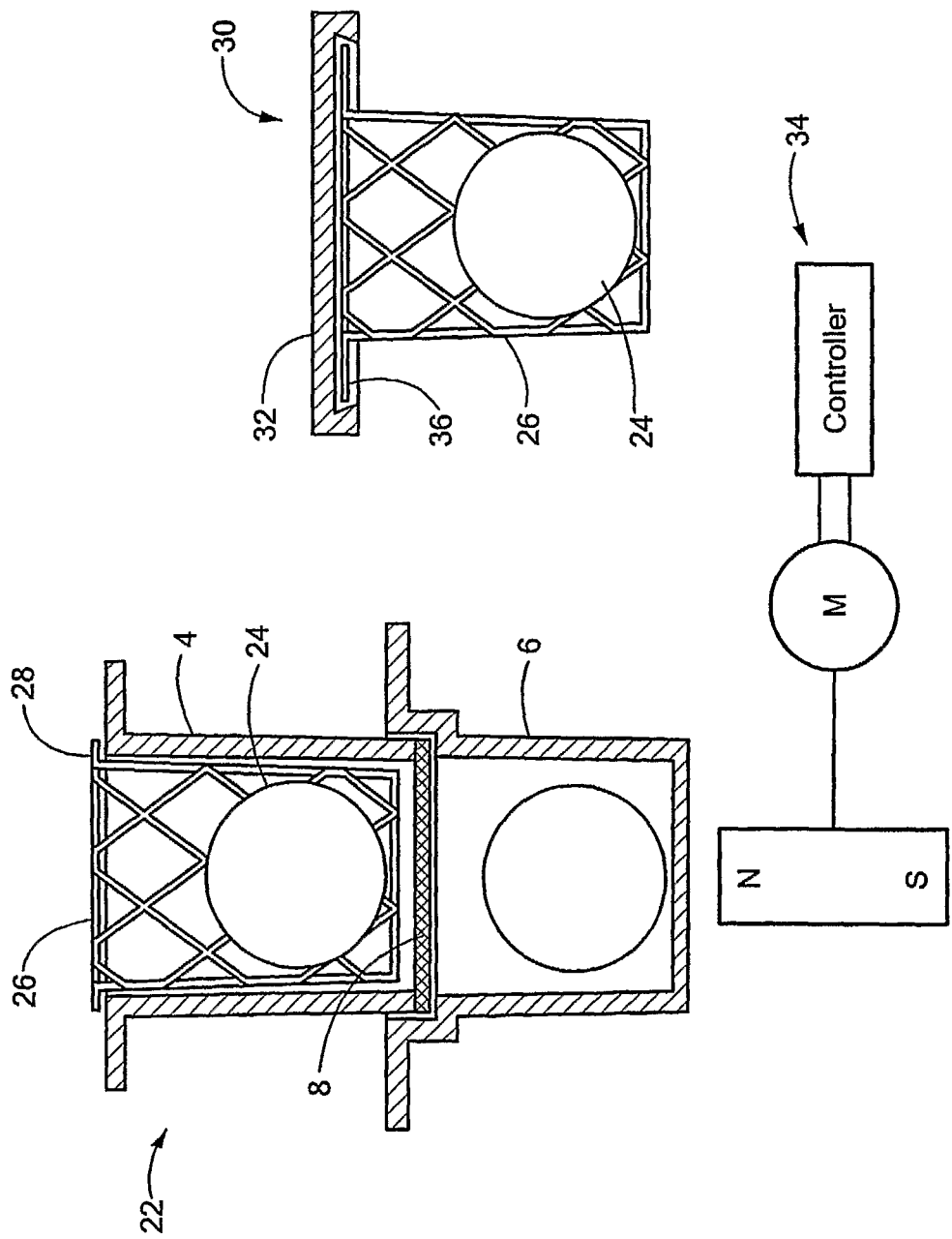
FIG. 2 is a partial representation of a device of the invention having stirring members disposed in both the insert well and receiving vessel.

FIG. 2 shows a partial representation of a device of the invention. In FIG. 2, a solution in the insert well 4 is capable of being stirred by a stirring member 24. The permeation device 22 comprises a receiving vessel 6 and an insert well 4. As described above, the insert well 4 has a porous support 8 disposed, attached or formed in a lower section of the well. The stirring member 24 is disposed in a strainer 26, which is disposed inside the insert well. The strainer bottom securely separates the stirring member 24 from the support 8 by, for example, being disposed between an interior of the well and stirring member 24.

The stirring member can, for example, be driven by magnetic or electromagnetic fields induced by an assembly such as the assembly 34, which comprises a magnet, motor and controller device. The components of the assembly 34 can operate as described above and may be incorporated into any one or all of the embodiments described herein. Exemplary types of assemblies are also generally described in U.S. Pat. No. 6,176,609, which is hereby incorporated by reference herein.

A stirring member 24 can be composed of any suitable material(s). The member can be inert such that it does not interfere with the assay. For example, a stirring member can be a magnetized or magnetizeable coated metal in which the coating is an inert polymer. A member can also be an inert metal such as stainless steel. A magnetized or magnetizeable member can be moved by, for example, a magnet. Alternatively, a member can be a glass or inert plastic bead that is moved using a vibrational body such as an orbital or linear plate shaker.

The strainer 26 can be provided with, for example, a flange 28 to suspend strainer 26 inside insert well 4 at a defined distance from support 8. The suspension of the strainer can be achieved by any suitable means such as a ring or other support feature inside or outside the insert well. The assembly 30 in the partial representation on the right in FIG. 2 shows the strainer 26 with the stirring member 24 disposed therein. The strainer can be fixed with respect to the lid 32 so as to trap the stirring member for ease of manufacture, transportation or use. The strainer can be fixed with respect to the lid by, for example, a constriction over the edge of a rim 36, although any other suitable approaches for fixing or positioning the strainer may be employed. Such exemplary approaches include bonding, heat-sealing, ultra-sonic welding or adhering the strainer to the lid.

As described above, the porous support 8 of FIG. 2 can also be adapted to receive a biological or biomimetic material disposed or grown on its upper or lower surface. Similarly, these materials can be disposed or grown in the pores of the support. For example, a non-living, biomimetic lipid-based membrane can be assembled on the support or in its pores. In one embodiment, a device of the invention comprises biological or biomimetic materials disposed or grown on an upper and lower surface of the porous support. Such an embodiment can be used for a co-culture assay. For co-culture assays, it is also contemplated that two different cell types are disposed or grown on the upper and lower surface, respectively, of the porous support.

Figure 3:
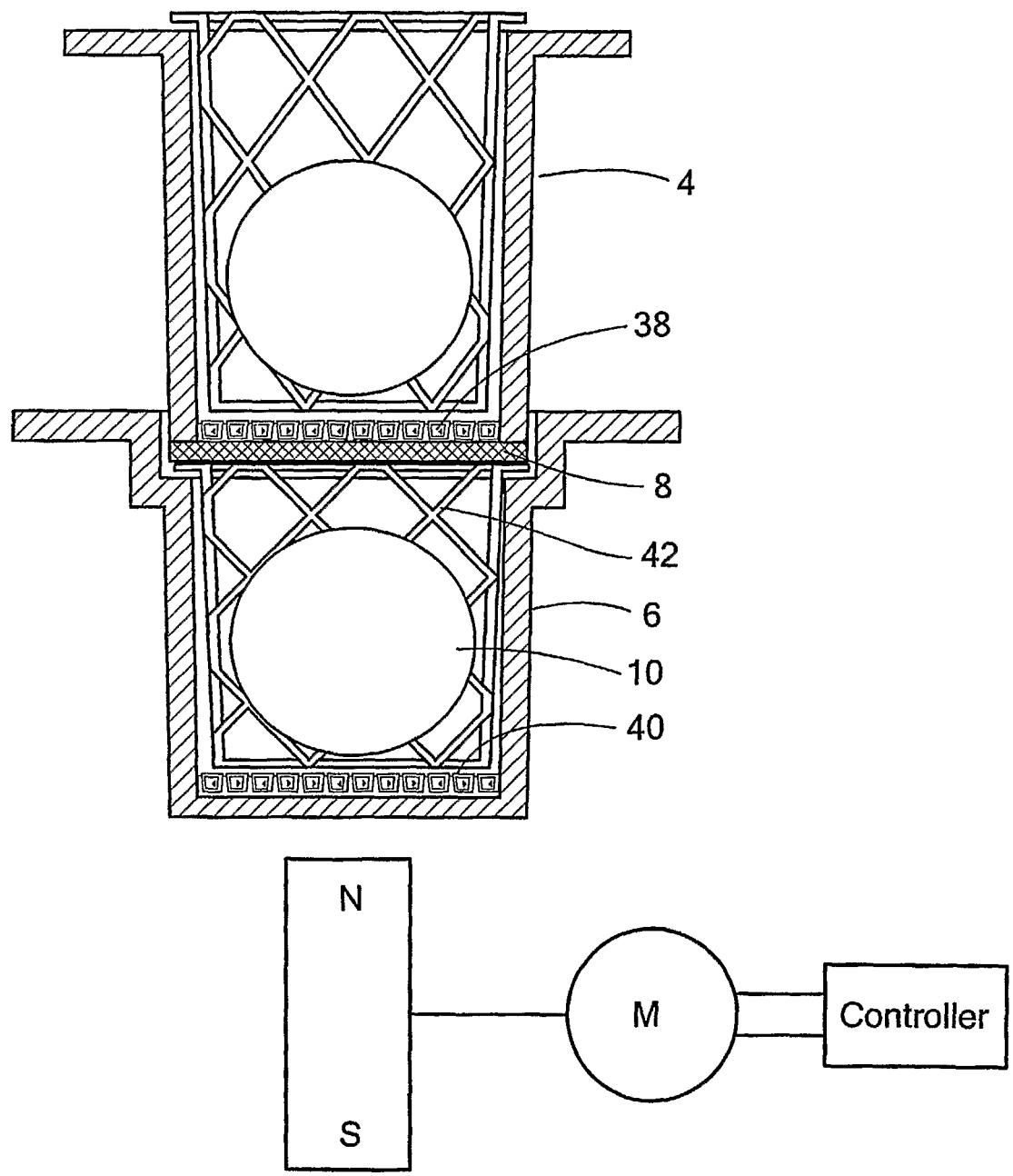
FIG. 3 is a partial representation of a device of the invention having cell cultures disposed or grown in both the insert well and receiving vessel.

It is also recognized that a similar assay may be carried out by, for example, having a first biological material such as a cell type disposed or grown on the porous support and a second material disposed or grown in the receiving vessel. FIG. 3 shows a partial representation of a permeation device having a first cell culture 38 deposited or grown on the porous support 8 in the lower section of the insert well 4 as well as a second cell culture 40 deposited or grown along a bottom of the receiving vessel 6. For such a co-culture assay, it can be particularly important to have a means by which to prevent such biological materials from being contacted by a stirring member, which could potentially damage the materials.

For example, FIG. 3 shows a second strainer 42 contained in the receiving vessel 6 to retain the stirring member 10 from contacting the second cell culture 40. As described above, the strainer can be fixed with respect to the vessel 6 by any suitable means. As also described above, a strainer can be disposed in the insert well 4 to prevent the stirring member therein from contacting the first cell culture 38 disposed or grown along an upper surface of the porous support 8. Exemplary strainers can be inert to common water-solvent mixtures. Such strainers are commonly formed from a non-magnetic mesh material or by using injection molding. Other typical methods or processes used to form a strainer as shown in FIGS. 2 and 3 are also applicable for a device of the invention.

Figure 4:
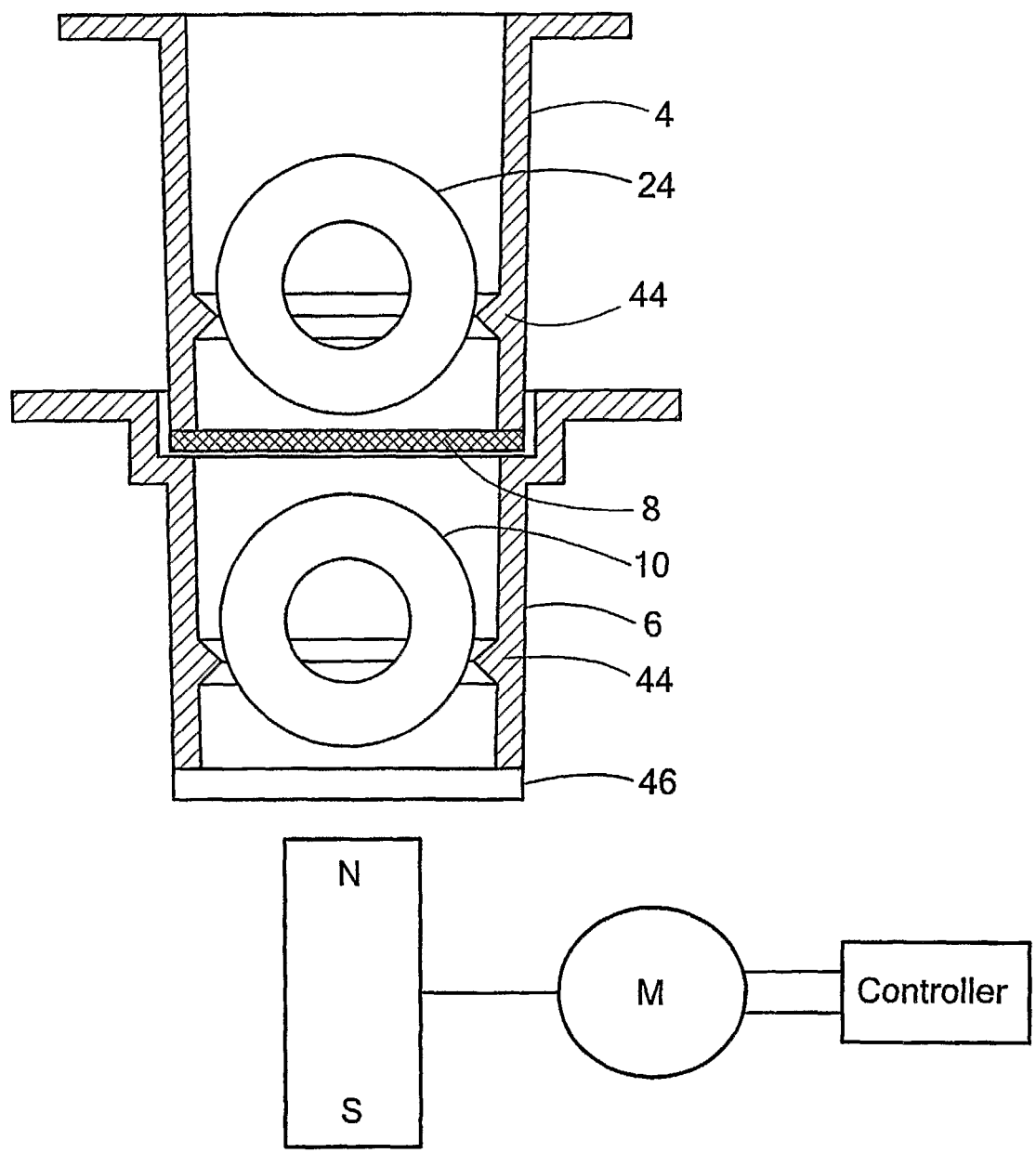
FIG. 4 is a partial representation of a device of the invention having constrictions extending into both the insert well and receiving vessel to retain one or more stirring members.

FIG. 4 shows a partial representation of a permeation device of the invention that is similar to those described above. The device in FIG. 4 can also include any type of constriction such as a ring-shaped constriction 44 in either or both the insert well 4 and receiving vessel 6. The constrictions 44 may, for example, be disposed about the diameter of the well 4 or vessel 6. Such constrictions can contain stirring members 10 and 24, which can feature exterior diameters slightly larger than the diameter of the corresponding constriction.

Exemplary stirring members 24 and 10 are shown in FIG. 4 as donut-shaped bits. Other exemplary stirring members include solid discs. The constrictions are intended such that the members will not make physical contact with the support 8 or the bottom of the well or vessel in any orientation. Moreover, constrictions 44 are also easy to incorporate into injection molds for the well or vessel, although any other suitable or conventional means of incorporating such constrictions into a device of the invention are possible.

As described above, the stirring members 24 and 10 shown in FIG. 4 can, for example, be donut-shaped to allow access to the porous support 8 or to allow light to be passed through the members into the bottom of the well 4 or vessel 6 for photometric analyses, which preferably occur when the members are not being moved. Such analyses can be performed without any sort of damage to the optical quality of the porous support or bottom of the well or vessel. Exemplary optical analyses can include ultraviolet (UV), infrared (IR), near IR, fluorescence spectroscopy or a combination thereof. In addition, a bottom portion of the receiving vessel 6 can be part of the vessel itself or be a suitable optical membrane 46 disposed, attached or formed in a leak-free manner in the vessel. Such leak-free manners or techniques include, for example, those that are described above.

Figure 5:
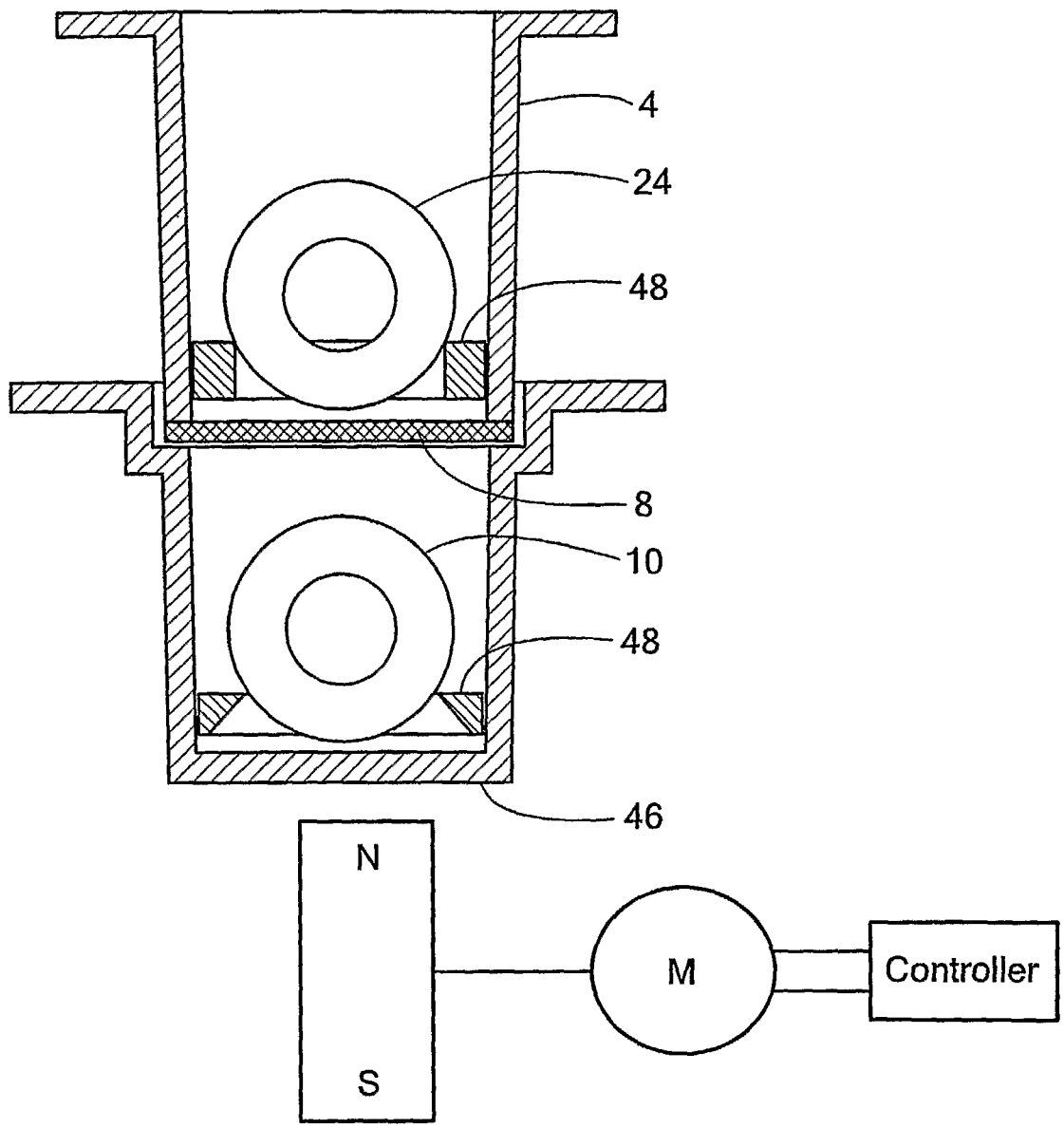
FIG. 5 is a partial representation of a device of the invention having retaining members disposed in both the insert well and receiving vessel to retain one or more stirring members.

FIG. 5 is a partial representation of another device embodiment of the invention. For example, ring members 48, which have an inside diameter smaller than an outside diameter of stirring members 10 and 24, in the insert well 4 and receiving vessel 6 prevent the stirring members from making physical contact with support 8 or an optical quality bottom 46 of the vessel 6. Such an embodiment of the invention can be particularly advantageous when the receiving vessel 6 is molded from an optical quality material that does not allow a constriction, for example, such as shown in FIG. 4, to be molded in place.

The ring members 48 can also prevent the stirring members from contacting any biological or biomimetic materials that are disposed or grown in the insert well or receiving vessel. The ring members in FIG. 5 are shown as examples of a retaining member or means, which is preferably used to retain the stirring members, although any other suitable or conventional means can be used with a device of the invention. Additional exemplary retaining members or means are also described herein.

Figure 6:
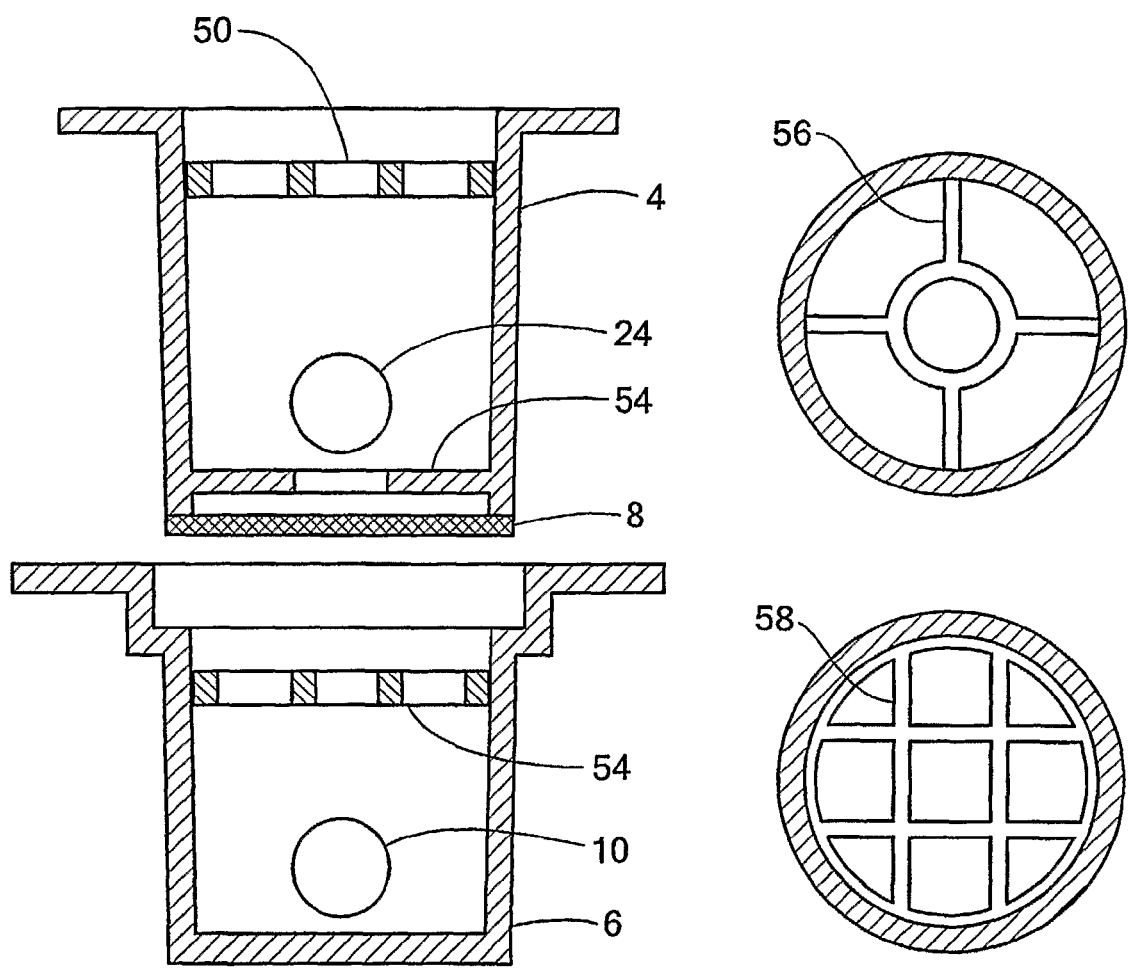
FIG. 6 is a partial representation of a device of the invention having retaining members disposed in both the insert well and receiving vessel to retain one or more stirring members.

FIG. 6 is a partial representation of a device of the invention featuring retaining members disposed in both the insert well and receiving vessel. For example, retaining members are shown as molded-in or inserted grids 54, fixed with respect to the insert well 4 and receiving vessel 6. Exemplary profiles for the grids are shown as structures 56 and 58 in the partial representations on the right in FIG. 6. The retaining members are intended to prevent stirring members 10 and 24 from making physical contact with porous support 8, while allowing a molecular entity to pass through the members and support.

For example, the retaining members 54 can prevent a stirring member 10, which may be a steel ball, from making physical contact with the support when the member 10 is raised. The stirring member can be raised and lowered to achieve stirring by using, for example, a magnetic field source located outside the vessel 6. In one embodiment, another retaining member 50, which is shown, for example, also as a grid, can be used to allow an additional well or vessel to be partially disposed in the insert well 4. Such an arrangement can be used for double-permeation assays. The invention also contemplates assays using a plurality of stackable insert wells and receiving vessels.

As described above, for a non-magnetic stirring member such as a glass bead or a dense inert polymer, movement of the member can be achieved by using a vibrational body such as linear or orbital shaker. The retaining members 50 and 54 shown in FIG. 6 serve equally well as guards for retaining such non-magnetic members within the insert well 4 or receiving vessel 6. A device of the invention can also employ several different means for moving a stirring member(s) during an assay. For example, a stirring member can be moved by a magnet and vibrational body simultaneously.

Figure 7:
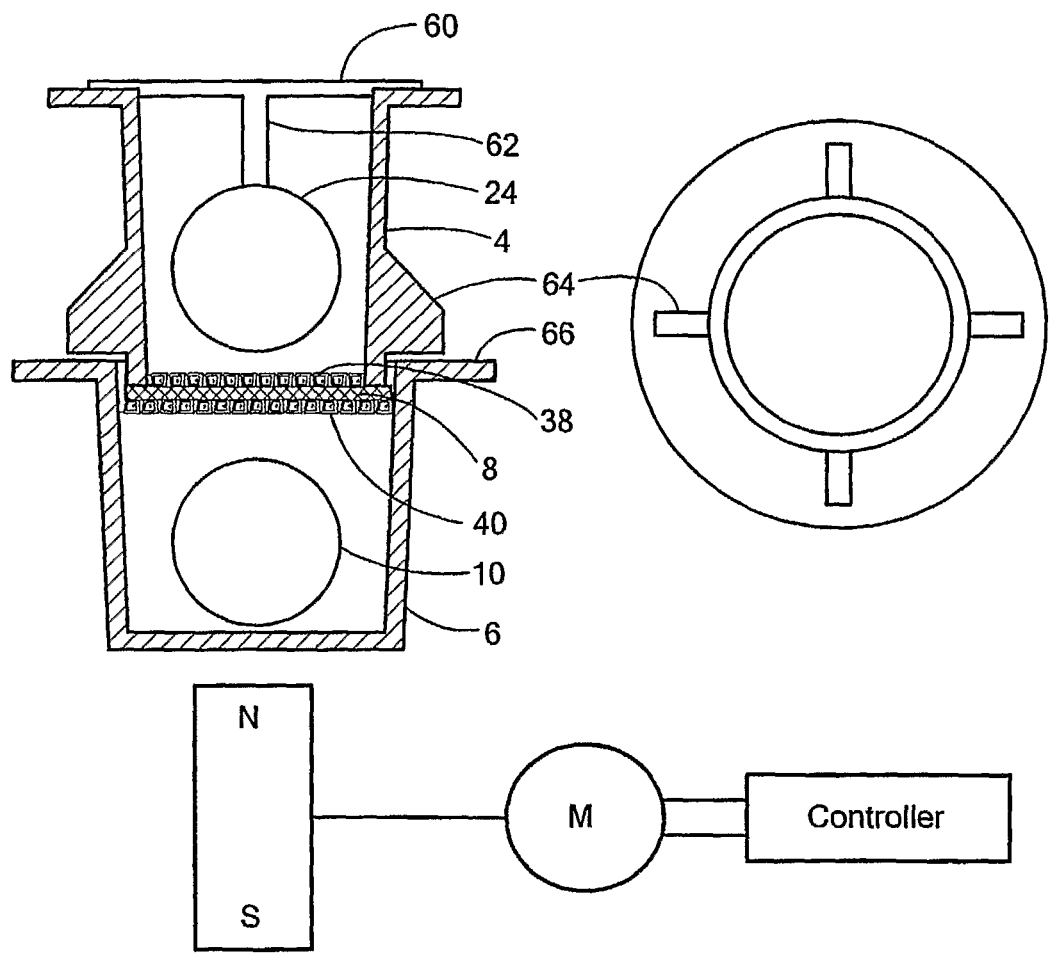
FIG. 7 is a partial representation of a device of the invention having cell cultures disposed or grown on an upper and lower surface of the porous structure.

The partial representation of a permeation device of the invention in FIG. 7 shows a co-culture assay. In particular, FIG. 7 shows a permeation device having a first cell culture 38 disposed or grown on the porous support 8 and a second cell culture 40 disposed or grown along a lower surface of the support. The first and second cell culture can be biological materials of the same or a different type. Alternatively, biomimetic materials can be disposed or assembled along an upper or lower surface of the porous support. In one embodiment, a combination of biological and biomimetic materials can be disposed or grown on both surfaces of the support. As described above, the support also allows biological or biomimetic materials to be disposed or grown in its pores.

As shown in FIG. 7, the insert well 4 and receiving vessel 6 are generally arranged as described above. FIG. 7 also shows the insert well partially disposed in the aperture of the vessel with a top surface 66 of the vessel supporting the well. The insert well 4 can comprise features that allow it to be suspended in the vessel 6 at a defined distance from the bottom of the vessel. For example, such features can be fins 64. Exemplary fins are shown in the partial representation on the right in FIG. 7, although any other suitable arrangement of fins or other features can alternatively be used.

The stirring member 10 in the vessel 6 can be similar to any of those that are described above. The member 24 in the insert well 4 can also be flexibly attached or coupled to an upper support structure 60 such that the member may move freely in a more or less horizontal plane, while being held securely at a given distance from the support 8. In one embodiment, the support structure 60 can be fixed with respect to the insert well. When the stirring members are moved, for example, via a rotating magnetic field(s), the member 24 can swing from side to side like, for example, a pendulum to enable solution agitation. Such a stirring member 24 can be coupled to the support structure 60, for example, by an extension 6, although any other suitable means may be used. The extension 62 can also be disposed or formed along with a coating for the member 24. In addition, the extension 62 can be formed as part of or separate from the support structure 60.

Figure 8:
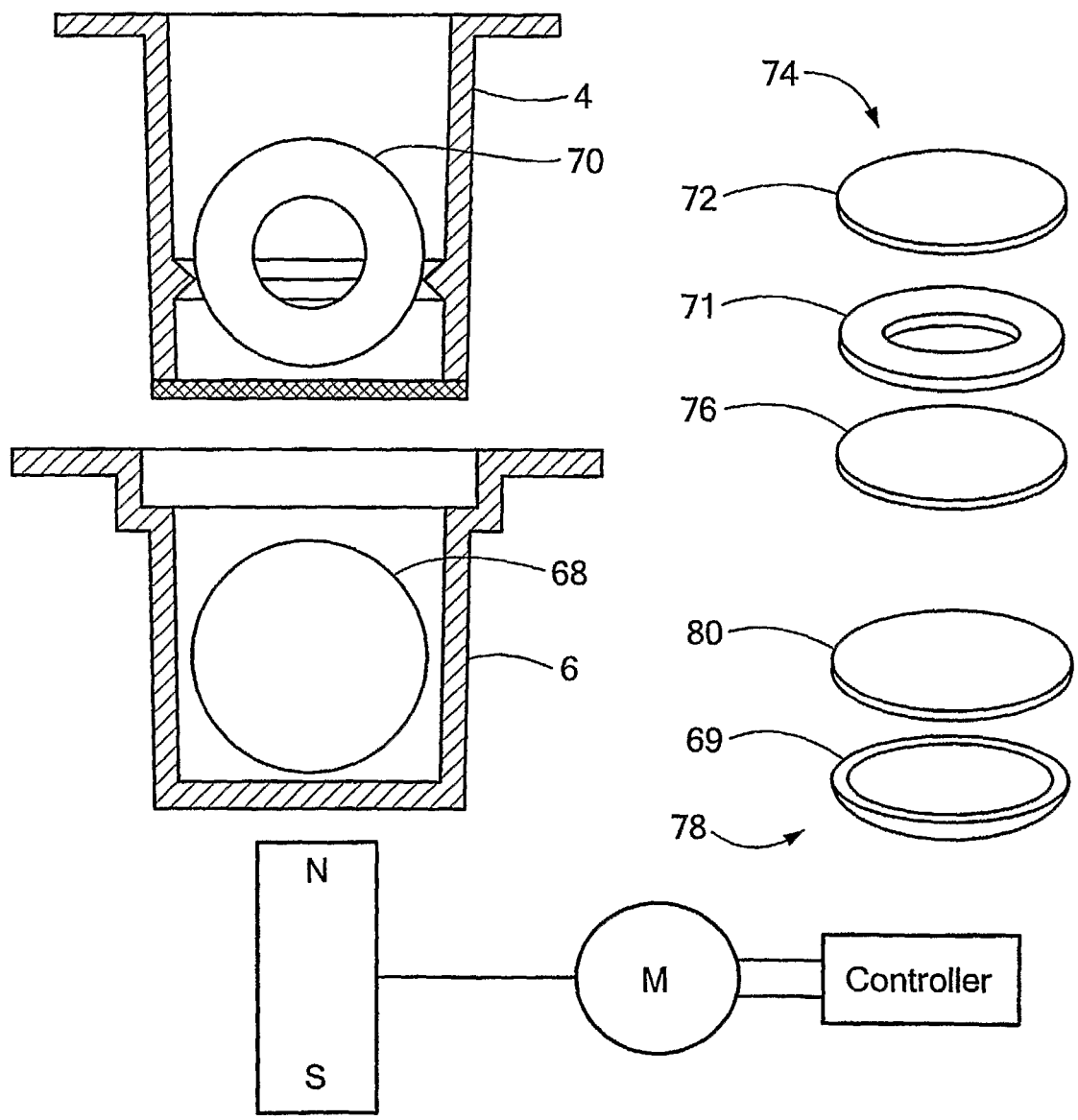
FIG. 8 is a partial representation of a device of the invention having stirring members that comprise a molecular entity disposed in both the insert well and receiving vessel.

FIG. 8 shows a partial representation of a permeation device of the invention similar to those described above. For example, the device may be any one of the embodiments described above or may incorporate features from any or all of the embodiments described herein. In one embodiment, the stirring members 68 and 70 disposed in the receiving vessel 6 and insert well 4, respectively, can have a means for holding an amount of a molecular entity in any form. The entity then permeates from the stirring member into solution. A molecular entity can be comprised by a stirring member in, for example, a powder, crystalline or pressed-pellet form. Preferably, only one of the stirring members comprises a molecular entity in which instance the other stirring member is optionally provided for solution agitation.

A molecular entity is held, for example, behind a hydrophilic filter membrane of the stirring member. For example, the assemblies 74 and 78 shown in the partial representations on the right in FIG. 8 exemplify different possible ways for having the entity comprised by a stirring member. In the assembly 74, a donut-shaped stirring member 71 provides space in its center to accommodate the entity. Filter material such as, for example, a hydrophilic material comprise covers 72 and 76, which are used to cover each side of the member.

In the assembly 78, the stirring member 69 is shaped as a shallow bowl providing space for the entity. In the assembly 78, a single cover 80 of, for example, filter material can be used to hold an entity. Preferably, the cover 80 is disposed on the member 69 to hold the entity therein. The covers 72, 76 and 80 can, for example, be comprised entirely of a filter material or include other materials that may be suitable for a molecular entity to permeate therethrough. Such stirring member assemblies allow for simultaneous or independent study of dissolution, solubility and permeation properties for a molecular entity.

Attaching or sealing one or more filter material covers to the stirring members can be performed by any suitable means such as, for example, solvent bonding, heat-sealing and ultrasonic welding. While FIG. 8 shows the stirring member 68 in the receiving vessel 6, it is understood that it could also be introduced in the insert well 4. Alternatively, the member 70 can be introduced into the vessel 6. Similarly, stirring members 69 and 71 can be disposed in either the insert well or receiving vessel. During, for example, dissolution or solubility based studies, the insert well 4 may not be necessary such as shown in FIG. 9.

Figure 9:
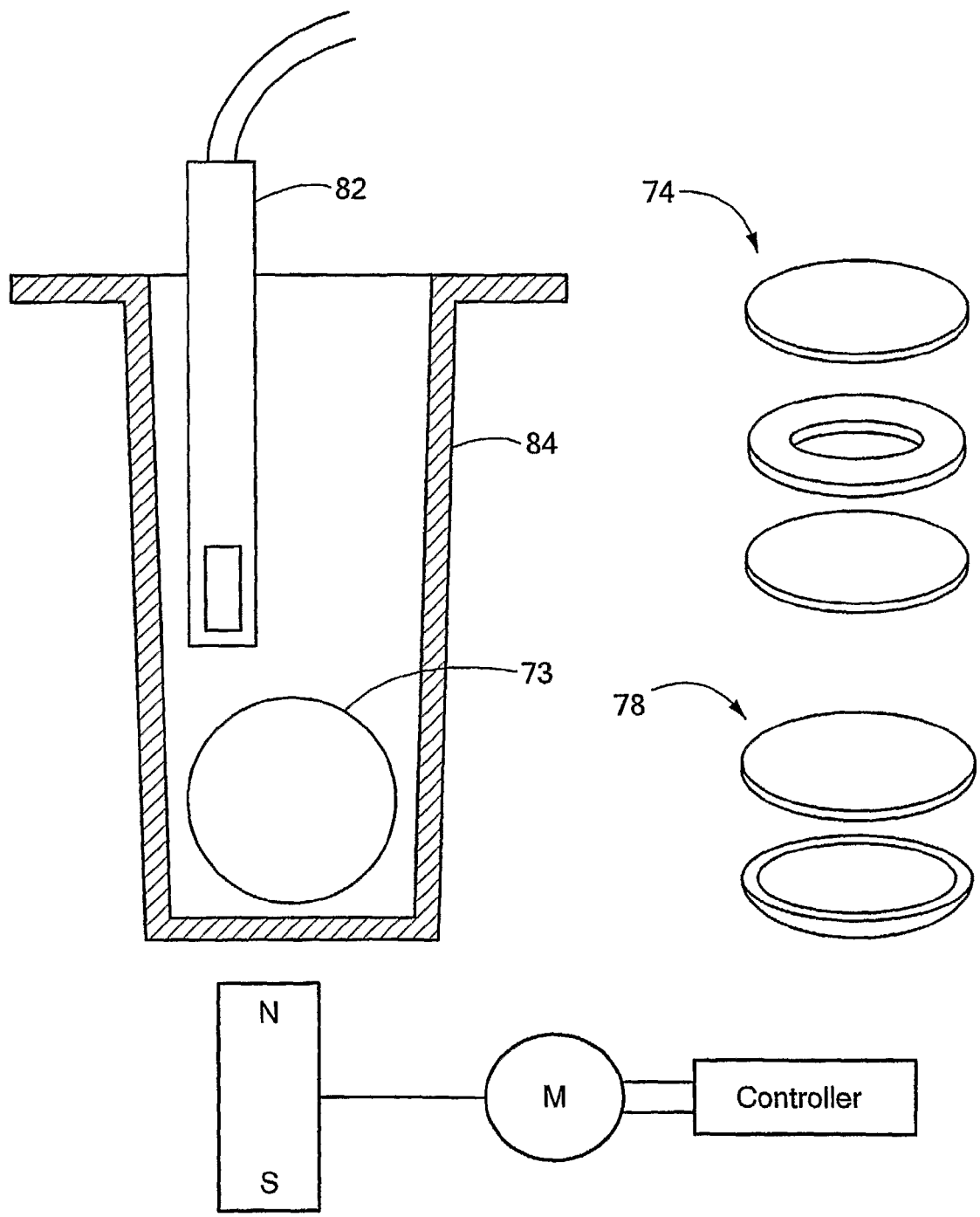
FIG. 9 is a partial representation of a device of the invention having a probe disposed in a receiving vessel with a stirring member that comprises a molecular entity.

FIG. 9 is a partial representation of a permeation device having a receiving vessel 84 with a sample-containing stirring member 73. The member 73 is intended to initially hold a molecular entity behind, for example, a filter such as a hydrophilic filter. The entity then permeates from the stirring member into solution. The filter can be a cover attached or sealed to the stirring member. Alternatively, the cover can include other materials with the filter material that may be suitable for a molecular entity to permeate therethrough. As described above, assemblies 74 and 78, shown in the partial representations on the right in FIG. 9, exemplify different ways to include a molecular entity in a stirring member.

FIG. 9 also shows a probe 82 inserted in the solution of the vessel 84 to permit measurement of, for example, the concentration of a molecular entity during dissolution of the entity. The probe may be based on a variety of principles such as, without limitation, thermal sensing, ion selective electrode technology, spectroscopic methods or a combination thereof. The latter may also be accomplished by using, for example, an optical quality receiving vessel to measure entity concentrations based on transmitted or transflected light during dissolution, which may not require the probe to come into direct contact with the device.

Figure 10:
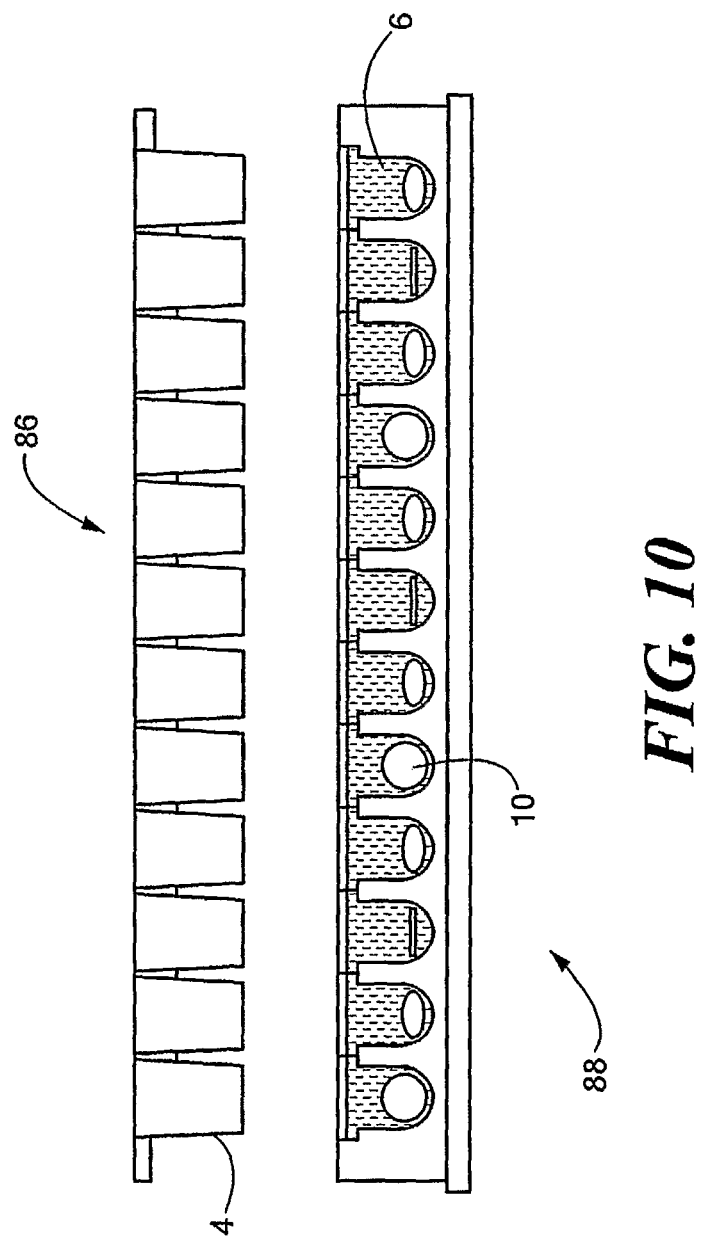
FIG. 10 is a partial representation of a donor and acceptor plate.

A partial representation of exemplary donor and acceptor microtitre plates is shown in FIG. 10. The microtitre plates are shown as a donor plate 86 and an acceptor plate 88. The donor plate comprises a plurality of insert wells 4. Moreover, the plate 88 comprises a plurality of receiving vessels 6. In another embodiment, a plurality of insert wells are comprised by an acceptor plate, while the donor plate comprises a plurality of receiving vessels. The donor and acceptor plates can be placed together to form a conventional permeation assay sandwich. FIG. 10 shows a stirring member 10 disposed in each of the receiving vessels 6. FIG. 10 also shows the stirring members in the vessels in different orientations.

An exemplary stirring member 10 can be a magnetized flipper. Such magnetized flippers can be simultaneously moved using any suitable means such as a magnet, motor and controller device or assembly as described above. The device or assembly may also have a speed dial setting calibrated so as to adjustably control the thicknesses of the individual aqueous boundary layers for each of the wells and vessels. The wells and vessels of the microtitre plates in FIG. 10 can also include or incorporate the variations of any or all other embodiments of the invention.

For example, an insert well or receiving vessel can include any type of stirring member that has been described above or any of those known in the art that are suitable for solution agitation. Similarly, for example, constrictions, retaining members, retaining means or a combination thereof can be included with any one of the embodiments described herein. Preferably, such plates as shown in FIG. 10 are microtitre plates of various formats that are adapted to be manipulated by an individual or a robotic device(s).

As described above, the invention also contemplates biological or biomimetic materials that are disposed in both the insert wells and the receiving vessels of the plates. In such a device of the invention, it may be particularly important to have a means by which to prevent these materials from being contacted by a stirring member, which could potentially damage the materials. Such means can include, for example, the constrictions, retaining members or retaining means described herein.

The present invention also provides a method for reducing boundary layer thicknesses. The method comprises providing one or more permeation devices of the invention. A stirring member(s) for the device is then moved to agitate a solution that preferably contains a molecular entity. The agitation of the solution can reduce the thickness of the boundary layers adjacent to the upper, lower or both surfaces of the porous support, which may include biological or biomimetic materials disposed thereon or therein. For example, boundary layer thicknesses are reduced by reducing the portion of solution that is substantially stagnant and adjacent to the porous support.

A reduction in boundary layer thicknesses can allow permeation of a molecular entity through the support, which comprises biological or biomimetic materials, to closely approximate in vivo absorption and transport conditions. The method also contemplates controlling the extent of agitation due to a stirring member(s) so as to adjustably change the boundary layer thicknesses adjacent to the upper, lower or both surfaces of the porous support. A method of the invention can also be carried out with a plurality of vessels or wells incorporated into donor or acceptor plates as described above.

The example herein is provided to illustrate advantages of the present invention that have not been previously described and to further assist a person of ordinary skill in the art with using a permeation device according to the invention. The example can include or incorporate any of the variations or embodiments of the invention described above. The embodiments described above may also further each include or incorporate the variations of any or all other embodiments of the invention.

For example, an insert well or receiving vessel can include any type of stirring member that has been described above or any of those known in the art that are suitable for solution agitation. Similarly, for example, constrictions, retaining members or retaining means or a combination thereof can be included with any one of the embodiments described herein. The following example is not intended in any way to otherwise limit the scope of the disclosure as provided herein.

EXAMPLE

Fifty five different molecular entities were used for the present example. These entities included 2-naphthoic acid, 4'N-Et-3'-Me-ciprofloxacin, 4'N-Et-3'-Et-ciprofloxacin, astemizole, 4'N—Pr-3'-Me-ciprofloxacin, acebutolol, amlodipine-maleate, antipyrine, 3-hydroxyphenylacetic acid, ergonovine, benzoic acid, diltiazem-hydrochloric acid (HCl), desipramine-HCl, phenazopyridine-HCl, diclofenac-sodium (Na), flurbiprofen, fluvoxamine, ibuprofen, imipramine-HCl, ketoprofen, lansoprazole, protriptyline-HCl, naproxen, nortriptyline-HCl, warfarin, nalidixic acid, naringenin, nicardipine, ondansetron, oxprenolol, phenytoin-Na, pindolol, propranolol-HCl, piroxicam, prazosin-HCl, probenecid, progesterone, quinine-HCl, salicylic acid, tiamdipine, timolol-maleate, zimelidine, tamoxifen[1], terfenadine[1], amiodarone-HCl[1], miconazole-nitrate[1], itraconazole[1], alprenolol-HCl[2], chlorpromazine-HCl[2], gemfibrozil[2], indomethacin[2], primaquine-diphosphate[2], verapamil-HCl[2], metoprolol-tartrate[2] and promethazine-HCl[2].

The above entities footnoted as "1" were insoluble in an aqueous buffer such that permeability measurements were conducted with the addition of 20 percent acetonitrile to the buffer. Additionally, those molecular entities that are footnoted as "2" had permeability measurements obtained in an aqueous buffer and a buffer having 20 percent acetonitrile added thereto. For this example, a PAMPA Evolution instrument from pION INC of Woburn, Mass. 01801 was used. A DOUBLE-SINK (pION INC of Woburn, Mass. 01801) GIT-0 lipid was also used as the material for the porous support, described below, to form a permeation barrier. A GUT-BOX (pION INC of Woburn, Mass. 01801) was also employed to provide stirring and for environmental control.

Solution pH was adjusted using a universal buffer as well as a buffer solution having a pH of 7.4 and containing a chemical scavenger to simulate serum proteins, which can be obtained from pION INC of Woburn, Mass. 01801. Donor and acceptor microtitre plates with 96 compartments were also employed for this example. The acceptor plate was obtained from Millipore Corporation of Billerica, Mass. 01821. The porous supports between the plate compartments had thicknesses of 125 µm and a pore size of 0.45 µm.

The $P_e$ of each entity was determined in a range of pH from about 3 to 10, using approximately equally spaced pH values to ensure obtaining results both above and below the effective ionization constant ($pK_a^{FLUX}$) value for the entities as generally described by Avdeef, "Absorption and Drug Development," Wiley Interscience, pp. 116-246 (2003). This approach for determining $P_e$ is often referred to as the $pK_a^{FLUX}$ method.

$pK_a^{FLUX}$ refers to the pH value where the resistance to transport across a permeation barrier is 50 percent due to the aqueous boundary layers and 50 percent due to the barrier. The donor solution samples, with each sample being about 50 micromolar (µM), were varied in pH, while the acceptor solutions had a consistent pH of about 7.4. As indicated above, the acceptor solutions contained a surfactant in order to mimic some of the function of serum proteins.

When not being stirred, a PAMPA sandwich was formed and permitted to incubate in the GUT-BOX at about 23° C. for up to several hours in an atmosphere saturated in humidity and scrubbed free of oxygen and carbon dioxide. Preferably, incubation was performed for up to about four hours. As described above, FIG. 10 shows a partial representation of exemplary donor and acceptor plates for a PAMPA sandwich. For example, the stirring members in FIG. 10 can be magnetized flippers that are controlled by a magnetic stirrer in the GUT-BOX, which causes the members to rotate about a horizontal axis. A speed dial for the magnetic stirrer, as described above, can be calibrated in units of thickness of the expected boundary layer rather than as standard units such as rpm. For example, such a calibration was based on 36 $P_u$ values of 14 different molecular entities at rotational speeds from about 49 to 622 rpm.

After a permeation time in the GUT-BOX was reached, the PAMPA sandwich could then be separated and the donor and acceptor compartments studied for the amount of entity present. The amount of entity present was determined from UV measurements compared to UV spectra obtained from reference standards. The reference UV spectra were performed in a range from about 230 to 500 nanometers (nm). Moreover, mass balance was used to determine the amount of material retained by the porous support and DOUBLE-SINK GIT-0 lipid as generally described by Avdeef et al., Eur. J. Pharm. Sci., 14, pp. 271-280 (2001).

Donor to acceptor compartment $P_e$ was also determined as described above for a range of pH from 3 to 10 using approximately equally spaced pH values for the $pK_a^{FLUX}$ method. The determination of $P_e$ also accounted for the porous support area and its porosity. In particular, the support area of 0.3 centimeters squared (cm$^2$) was multiplied by the apparent porosity ($\epsilon_a$) of the support, which was about 0.76, such as generally described by Nielsen et al., Eur. J. Pharm. Sci., 22, pp. 33-41 (2004). Accounting for support area and its apparent porosity ensures that the aqueous boundary layer thicknesses determined from the PAMPA would be comparable to assays using different supports of various sizes and porosities.

Tables 1 to 5 includes the $P_u$ values of 53 ionizable entities determined by the $pK_a^{FLUX}$ method described above. These entities were each sufficiently lipophilic such that their intrinsic permeability coefficients ($P_o$) were nearly equal to or greater than $P_u$, which is a requirement of the $pK_a^{FLUX}$ method. The majority of the data in Tables 1 through 5 is from unstirred assays and those stirred at about 186 rpm. The $P_u$ values of propranolol, desipramine, imipramine and verapamil were determined at five different speeds of 0, 49, 118, 186 and 622 rpm. Moreover, metoprolol and naproxen were characterized at four different speeds. Tamoxifen, chlorpromazine, indomethacin, itraconazole, ketoprofen, miconazole, probenecid and nifedipine were also studied in stirred solutions. The maximum speed used for these entities was 622 rpm.

Again, several entities were studied in a buffer comprising about 20 percent acetonitrile. These entities are footnoted as "1" in Tables 1 through 5. Given the known fractional −⅙ power dependence of $P_u$ on solution viscosity, the use of an acetonitrile cosolvent did not substantially affect the assays such as shown by chlorpromazine at 622 rpm, which was studied both with and without the cosolvent. Tables 1 through 5 are provided below with Table 1 at 0 rpm, Table 2 stirred at 49 rpm, Table 3 stirred at 118 rpm, Table 4 stirred at 186 rpm and Table 5 stirred at 622 rpm. Tables 1 through 5 also include the standard deviation (SD) of determined $P_u$ values.

TABLE 1

| Molecular Entity | MW | Daq (cm$^2$ s$^{-1}$) | $P_u$ | SD | h (µm) |
|---|---|---|---|---|---|
| 4'N-Bu-3'-Me-ciprofloxacin | 401.5 | 4.9 × 10$^{-6}$ | 23 | 3 | 2133 |
| 4'N-Et-3'-Me-ciprofloxacin | 373.4 | 5.0 × 10$^{-6}$ | 53 | 28 | 945 |
| 4'N-Pr-3'-Me-ciprofloxacin | 387.4 | 4.9 × 10$^{-6}$ | 40 | 24 | 1236 |
| 3-hydroxyphenylacetic acid | 152.1 | 7.6 × 10$^{-6}$ | 50 | 12 | 1524 |
| Acebutolol | 336.4 | 5.3 × 10$^{-6}$ | 63 | 26 | 837 |
| Alprenolol | 249.4 | 6.0 × 10$^{-6}$ | 32 | 6 | 889 |
| Benzoic | 122.1 | 8.4 × 10$^{-6}$ | 86 | 8 | 983 |
| Chlorpromazine | 318.9 | 5.4 × 10$^{-6}$ | 32 | 3 | 1713 |
| Desipramine | 266.4 | 5.9 × 10$^{-6}$ | 48 | 3 | 1227 |
| Diclofenac | 296.2 | 5.6 × 10$^{-6}$ | 41 | 5 | 1362 |
| Diltiazem | 378.1 | 5.0 × 10$^{-6}$ | 40 | 6 | 1244 |
| Ergonovine | 325.4 | 5.3 × 10$^{-6}$ | 25 | 4 | 2113 |
| Flurbiprofen | 244.3 | 6.1 × 10$^{-6}$ | 70 | 6 | 878 |
| Gemfibrozil | 250.0 | 6.0 × 10$^{-6}$ | 53 | 12 | 1135 |
| Ibuprofen | 206.3 | 6.6 × 10$^{-6}$ | 40 | 5 | 1666 |
| Imipramine | 280.4 | 5.7 × 10$^{-6}$ | 44 | 4 | 1293 |
| Indomethacin | 357.8 | 5.1 × 10$^{-6}$ | 32 | 1 | 1604 |
| Ketoprofen | 254.3 | 6.0 × 10$^{-6}$ | 37 | 3 | 1637 |
| Lansoprazole | 369.0 | 5.0 × 10$^{-6}$ | 35 | 17 | 1462 |
| Metoprolol | 267.4 | 5.9 × 10$^{-6}$ | 61 | 6 | 953 |
| Nalidixic acid | 232.2 | 6.2 × 10$^{-6}$ | 44 | 5 | 1429 |
| Naproxen | 230.3 | 6.3 × 10$^{-6}$ | 64 | 6 | 983 |
| Naringenin | 272.3 | 5.8 × 10$^{-6}$ | 39 | 6 | 1496 |
| Nortriptyline | 263.4 | 5.9 × 10$^{-6}$ | 60 | 11 | 991 |

TABLE 1-continued

| Molecular Entity | MW | Daq (cm² s⁻¹) | $P_u$ | SD | h (μm) |
|---|---|---|---|---|---|
| Ondansetron | 293.4 | 5.6 × 10⁻⁶ | 59 | 10 | 949 |
| Oxprenolol | 265.4 | 5.9 × 10⁻⁶ | 67 | 9 | 882 |
| Phenazopyridine | 213.2 | 6.5 × 10⁻⁶ | 29 | 3 | 2264 |
| Phenytoin | 252.3 | 6.0 × 10⁻⁶ | 26 | 4 | 2277 |
| Pindolol | 248.3 | 6.1 × 10⁻⁶ | 28 | 11 | 2194 |
| Piroxicam | 331.4 | 5.3 × 10⁻⁶ | 31 | 3 | 1688 |
| Prazosin | 383.4 | 5.0 × 10⁻⁶ | 38 | 7 | 1305 |
| Primaquine | 259.4 | 5.9 × 10⁻⁶ | 30 | 7 | 1992 |
| Probenecid | 285.4 | 5.7 × 10⁻⁶ | 43 | 8 | 1336 |
| Promethazine | 284.4 | 5.7 × 10⁻⁶ | 50 | 4 | 1147 |
| Propranolol | 259.3 | 5.9 × 10⁻⁶ | 41 | 3 | 1455 |
| Quinine | 324.4 | 5.4 × 10⁻⁶ | 24 | 2 | 2231 |
| Salicylic acid | 138.1 | 7.9 × 10⁻⁶ | 37 | 7 | 2151 |
| Timolol | 316.2 | 5.4 × 10⁻⁶ | 67 | 28 | 809 |
| Verapamil | 454.6 | 4.6 × 10⁻⁶ | 46 | 3 | 994 |
| Warfarin | 308.3 | 5.5 × 10⁻⁶ | 70 | 12 | 789 |

TABLE 2

| Molecular Entity | MW | Daq (cm² s⁻¹) | $P_u$ | SD | h (μm) |
|---|---|---|---|---|---|
| Desipramine | 266.4 | 5.9 × 10⁻⁶ | 367 | 27 | 159 |
| Imipramine | 280.4 | 5.7 × 10⁻⁶ | 337 | 33 | 146 |
| Metoprolol | 267.4 | 5.9 × 10⁻⁶ | 177 | 80 | 335 |
| Propranolol | 259.3 | 5.9 × 10⁻⁶ | 369 | 38 | 160 |
| Verapamil | 454.6 | 4.6 × 10⁻⁶ | 383 | 80 | 130 |

TABLE 3

| Molecular Entity | MW | Daq (cm² s⁻¹) | $P_u$ | SD | h (μm) |
|---|---|---|---|---|---|
| Desipramine | 266.4 | 5.9 × 10⁻⁶ | 747 | 39 | 78 |
| Imipramine | 280.4 | 5.7 × 10⁻⁶ | 786 | 93 | 69 |
| Metoprolol | 267.4 | 5.9 × 10⁻⁶ | 490 | 237 | 121 |
| Naproxen | 230.3 | 6.3 × 10⁻⁶ | 493 | 65 | 129 |
| Propranolol | 259.3 | 5.9 × 10⁻⁶ | 601 | 80 | 101 |
| Verapamil | 454.6 | 4.6 × 10⁻⁶ | 681 | 31 | 69 |

TABLE 3

| Molecular Entity | MW | Daq (cm² s⁻¹) | $P_u$ | SD | h (μm) |
|---|---|---|---|---|---|
| 2-naphthoic acid | 172.2 | 7.2 × 10⁻⁶ | 595 | 22 | 121 |
| Alprenolol | 249.4 | 6.0 × 10⁻⁶ | 1310 | 104 | 46 |
| Alprenolol[1] | 249.4 | 6.0 × 10⁻⁶ | 2530 | 240 | 24 |
| Amlodipine | 403.9 | 4.8 × 10⁻⁶ | 1380 | 25 | 35 |
| Astemizole | 458.6 | 4.6 × 10⁻⁶ | 746 | 104 | 61 |
| Chlorpromazine | 318.9 | 5.4 × 10⁻⁶ | 1430 | 88 | 38 |
| Desipramine | 266.4 | 5.9 × 10⁻⁶ | 801 | 85 | 73 |
| Diclofenac | 296.2 | 5.6 × 10⁻⁶ | 1390 | 353 | 40 |
| Diltiazem | 378.1 | 5.0 × 10⁻⁶ | 904 | 168 | 55 |
| Flurbiprofen | 244.3 | 6.1 × 10⁻⁶ | 2260 | 301 | 27 |
| Gemfibrozil | 250.0 | 6.0 × 10⁻⁶ | 1370 | 69 | 44 |
| Imipramine | 280.4 | 5.7 × 10⁻⁶ | 1240 | 94 | 46 |
| Indomethacin | 357.8 | 5.1 × 10⁻⁶ | 1040 | 180 | 49 |
| Indomethacin[1] | 357.8 | 5.1 × 10⁻⁶ | 926 | 22 | 55 |
| Itraconazole[1] | 705.6 | 3.7 × 10⁻⁶ | 1360 | 184 | 28 |
| Ketoprofen | 254.3 | 6.0 × 10⁻⁶ | 1750 | 539 | 34 |
| Metoprolol | 267.4 | 5.9 × 10⁻⁶ | 693 | 64 | 84 |
| Miconazole[1] | 416.1 | 4.8 × 10⁻⁶ | 1690 | 243 | 28 |
| Naproxen | 230.3 | 6.3 × 10⁻⁶ | 1320 | 375 | 48 |
| Nicardipine | 479.5 | 4.5 × 10⁻⁶ | 1250 | 109 | 36 |
| Ondansetron | 293.4 | 5.6 × 10⁻⁶ | 6949 | 396 | 59 |
| Phenazopyridine | 213.2 | 6.5 × 10⁻⁶ | 1340 | 690 | 48 |
| Pindolol | 248.3 | 6.1 × 10⁻⁶ | 1440 | 660 | 42 |
| Primaquine[1] | 259.4 | 5.9 × 10⁻⁶ | 2470 | 522 | 24 |
| Probenecid | 285.4 | 5.7 × 10⁻⁶ | 1030 | 187 | 55 |

TABLE 3-continued

| Molecular Entity | MW | Daq (cm² s⁻¹) | $P_u$ | SD | h (μm) |
|---|---|---|---|---|---|
| Promethazine | 284.4 | 5.7 × 10⁻⁶ | 1240 | 244 | 46 |
| Promethazine[1] | 284.4 | 5.7 × 10⁻⁶ | 1440 | 543 | 40 |
| Propranolol | 259.3 | 5.9 × 10⁻⁶ | 951 | 154 | 62 |
| Quinine | 324.4 | 5.4 × 10⁻⁶ | 905 | 58 | 59 |
| Tamoxifen[1] | 371.5 | 5.0 × 10⁻⁶ | 1120 | 234 | 45 |
| Tiamdipine | 435.5 | 4.7 × 10⁻⁶ | 951 | 38 | 49 |
| Timolol | 316.2 | 5.4 × 10⁻⁶ | 1640 | 206 | 33 |
| Verapamil | 454.6 | 4.6 × 10⁻⁶ | 697 | 65 | 66 |
| Verapamil[1] | 454.6 | 4.6 × 10⁻⁶ | 691 | 91 | 66 |

TABLE 3

| Molecular Entity | MW | Daq (cm² s⁻¹) | $P_u$ | SD | h (μm) |
|---|---|---|---|---|---|
| Amiodarone[1] | 172.2 | 7.2 × 10⁻⁶ | 595 | 22 | 121 |
| Chlorpromazine | 318.9 | 5.4 × 10⁻⁶ | 2940 | 349 | 18 |
| Chlorpromazine[1] | 318.9 | 5.4 × 10⁻⁶ | 2570 | 742 | 21 |
| Desipramine | 266.4 | 5.9 × 10⁻⁶ | 1980 | 314 | 30 |
| Fluvoxamine | 318.3 | 5.4 × 10⁻⁶ | 1520 | 380 | 36 |
| Gemfibrozil[1] | 250.0 | 6.0 × 10⁻⁶ | 1350 | 197 | 45 |
| Imipramine | 280.4 | 5.7 × 10⁻⁶ | 2720 | 220 | 21 |
| Indomethacin | 357.8 | 5.1 × 10⁻⁶ | 2910 | 609 | 18 |
| Itraconazole[1] | 705.6 | 3.7 × 10⁻⁶ | 2210 | 254 | 17 |
| Ketoprofen | 254.3 | 6.0 × 10⁻⁶ | 1110 | 122 | 54 |
| Metoprolol[1] | 267.4 | 5.9 × 10⁻⁶ | 1520 | 316 | 39 |
| Miconazole[1] | 416.1 | 4.8 × 10⁻⁶ | 1520 | 316 | 31 |
| Naproxen | 230.3 | 6.3 × 10⁻⁶ | 2040 | 209 | 31 |
| Probenecid | 285.4 | 5.7 × 10⁻⁶ | 1280 | 211 | 44 |
| Propranolol | 259.3 | 5.9 × 10⁻⁶ | 3110 | 313 | 19 |
| Protriptyline | 263.4 | 5.9 × 10⁻⁶ | 2150 | 518 | 27 |
| Tamoxifen[1] | 371.5 | 5.0 × 10⁻⁶ | 980 | 235 | 51 |
| Terfenadine[1] | 471.7 | 4.5 × 10⁻⁶ | 2440 | 85 | 18 |
| Verapamil | 454.6 | 4.6 × 10⁻⁶ | 3540 | 523 | 13 |
| Zimelidine | 317.2 | 5.4 × 10⁻⁶ | 1670 | 516 | 32 |

Also listed in Tables 1 through 5 are aqueous diffusivity ($D_{aq}$) values at about 25° C., which can be approximated from the empirical formula of $$\log D_{aq} = -4.113 - 0.4609 (\log MW)$$

This formula was generally described by Avdeef, "Absorption and Drug Development," Wiley Interscience, pp. 116-246 (2003). The boundary layer thickness (h) in Tables 1 through 5 can be determined by Fick's second law of diffusion, which is $$h = \frac{D_{aq}}{P_u}$$

Figure 11:
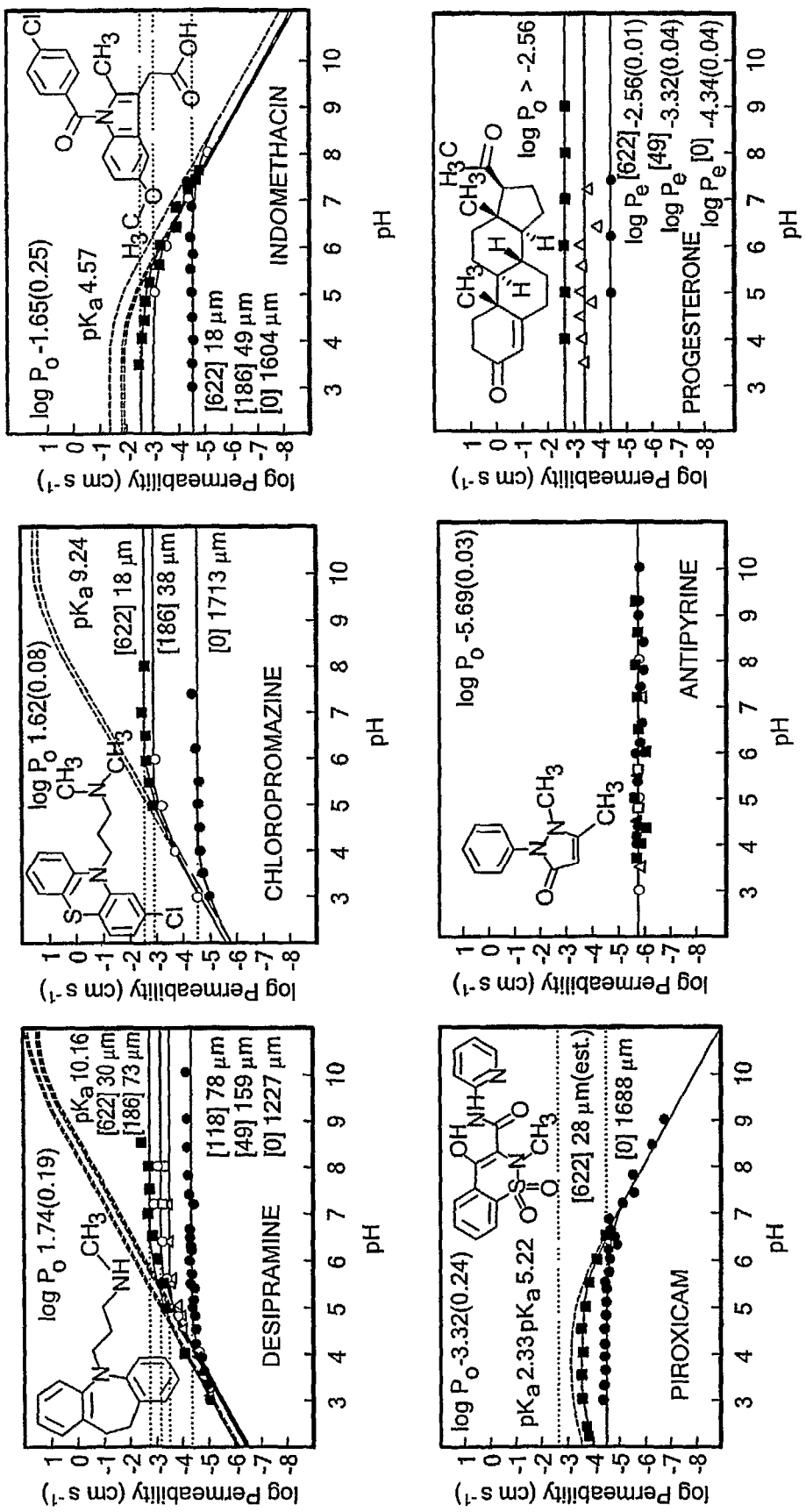
FIG. 11 shows six logarithm of effective permeability ($P_e$) versus pH plots of ionizable acid and base molecular entities measured at different stirring speeds.

FIG. 11 shows six logarithm of $P_e$ versus pH plots of ionizable acid and base molecular entities measured at different stirring speeds. Solid line curves were fitted to the measured points according to the equation $$\log P_e = \log P_e^{MAX} - \log(10^{+(pH-pK_a^{FLUX})} + 1)$$

for monoprotic acids and the equation $$\log P_e = \log P_e^{MAX} - \log(10^{-(pH-pK_a^{FLUX})} + 1)$$

for monoprotic bases such as generally described by Avdeef et al., Eur. J. Pharm. Sci., 22, pp. 365-374 (2004) in which $P_e^{MAX}$ relates to a value less than $P_e$ given that boundary layer thicknesses cannot be entirely eliminated by stirring.

The dotted horizontal lines on top of the solid line curves in FIG. 11 indicate the actual values of $P_u$. The dashed curves were calculated from knowledge of a true aqueous $pK_a$ and a refined $P_o$, which was based on a curve-fit according to an equation(s) similar to those above for monoprotic acids and bases. The tops of the dashed curves correspond to values of the logarithm of $P_o$. The points in the horizontal solid line domains indicate transport that is almost entirely boundary layer limited. The points along the horizontal solid line domains also show sensitivity to the selected stirring speed.

Figure 12:
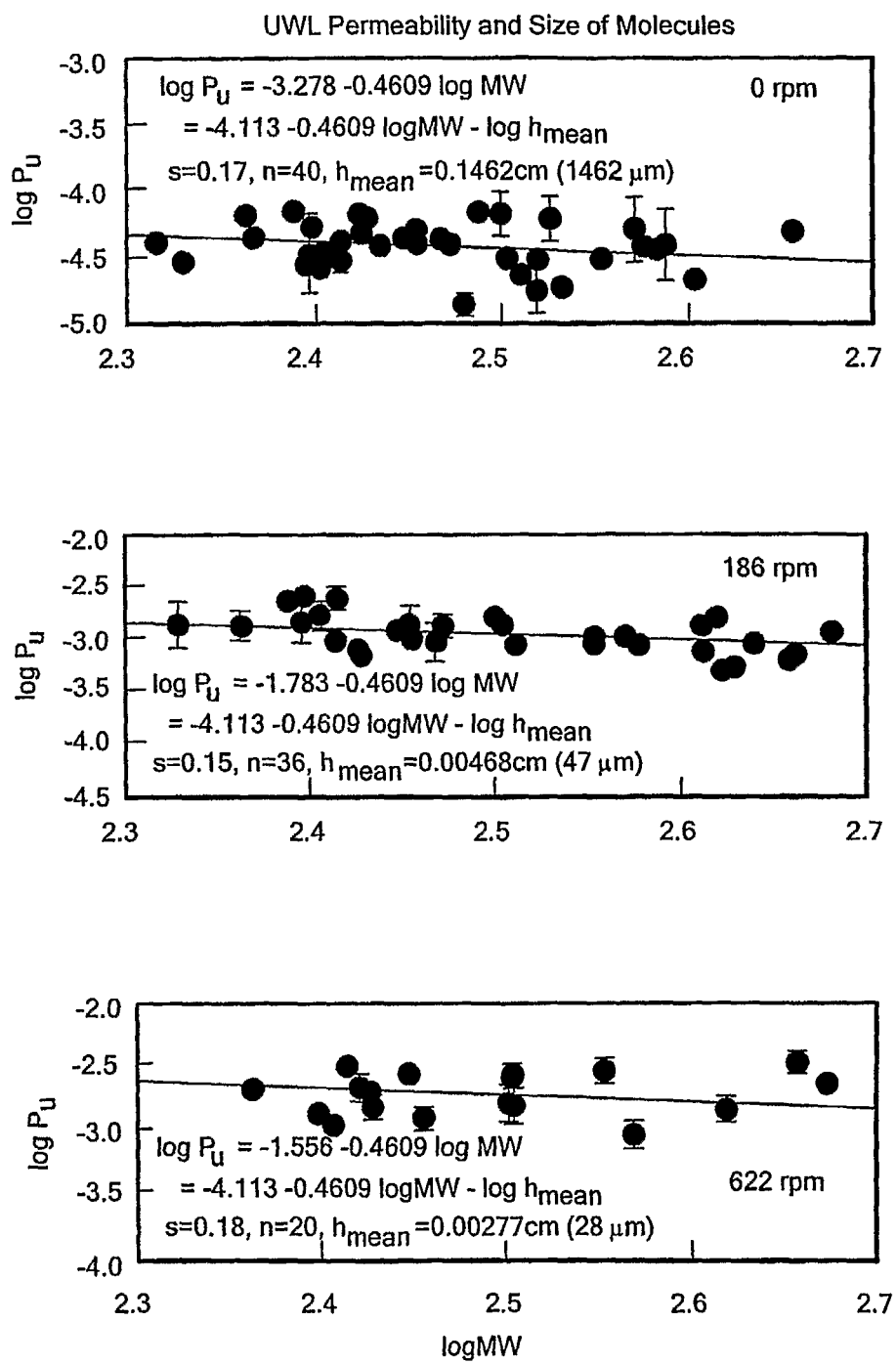
FIG. 12 shows plots of the logarithm of boundary layer permeability ($P_u$) versus the logarithm of molecular weight (MW) at stirring speeds of 0, 186 and 622 revolutions per minute (rpm)

Furthermore, FIG. 12 shows plots of the logarithm of $P_u$ versus the logarithm of MW at 0, 186 and 622 rpm. For each of the stirring speeds, the data were fitted to the empirical equation $$\log P_u = \log D_{aq} - \log h_{MEAN}$$

from which the empirical formula describe above can be substituted in order to yield $$\log P_u = -4.113 - 0.4609(\log MW) - \log h_{MEAN}$$

Thus, average boundary layer thicknesses ($h_{MEAN}$) can be determined based on a weighted regression analysis such that average thickness values of 1462 µm, 177 µm, 91 µm, 47 µm and 28 µm are based on stir speeds of 0 rpm, 49 rpm, 118 rpm, 186 rpm and 622 rpm, respectively.

Figure 13:
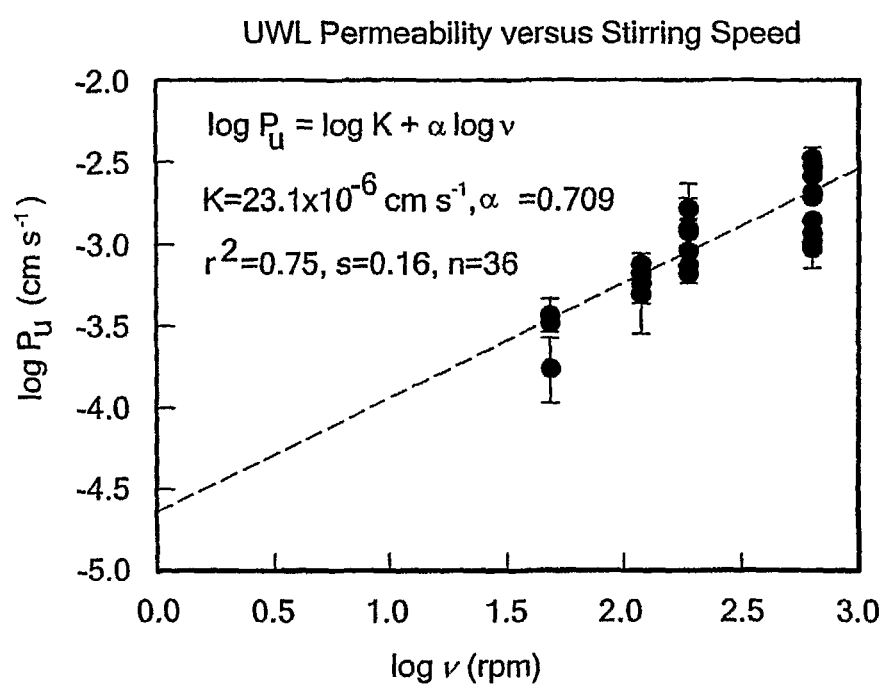
FIG. 13 is a plot of the logarithm of $P_u$ versus the logarithm of stirring speeds (v) for 36 different measurements based on 14 molecular entities.

$P_u$ values derived at various stirring speeds by using the $pK_a^{FLUX}$ method, as described above, were also subjected to a hydrodynamic analysis using the equation $$P_u = Kv^\alpha$$

in a logarithmic form. For example, FIG. 13 provides a plot of the logarithm of $P_u$ versus the logarithm of v comprising 36 measurements based on 14 molecular entities studied at several different stirring speeds. The intercept in such a plot is the logarithm of the stirring efficiency factor (K) with the slope being the hydrodynamic factor ($\alpha$). A regression analysis then describes the average hydrodynamic character of a stirred PAMPA sandwich.

K was determined by the regression analysis in FIG. 13 to be $23 \times 10^{-6}$ cm s$^{-1}$ and $\alpha$ was determined to be 0.71. The value of $\alpha$ is close to the value 0.8 reported by Adson et al., J. Pharm. Sci., 84, pp. 1197-1204 (1995), although the PAMPA K factor is about 6 times higher than the previous maximum reported value. This result is significant as it means that for a given stirring speed, the thicknesses of the boundary layers in a PAMPA are dramatically less than in the most efficiently stirred Caco-2 type cell assay.

Figure 14:
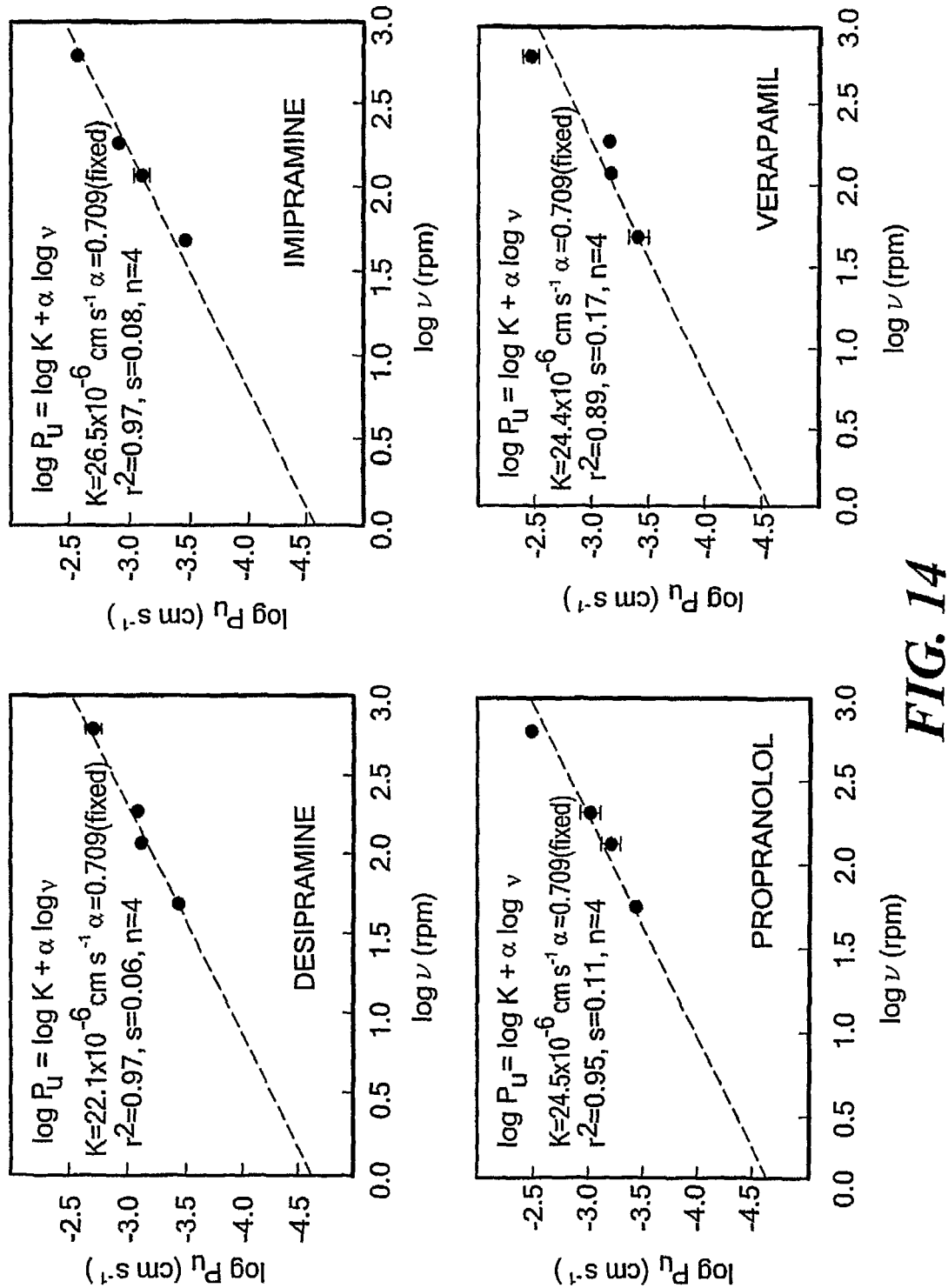
FIG. 14 shows plots of the logarithm of $P_u$ of four molecular entities versus the logarithm of v.

In addition, FIG. 14 shows the individual behavior of four different molecular entities that were studied at various stirring speeds. Due to the limited number of measured points for each of the molecular entities and the narrow range of values of the logarithm of v, the shown fitting constrained $\alpha$ to an average value of about 0.71. For example, as shown in FIG. 14, the individual K values ranged from about $22 \times 10^{-6}$ cm s$^{-1}$ for the entity desipramine to about $27 \times 10^{-6}$ cm s$^{-1}$ for imipramine.

Figure 15:
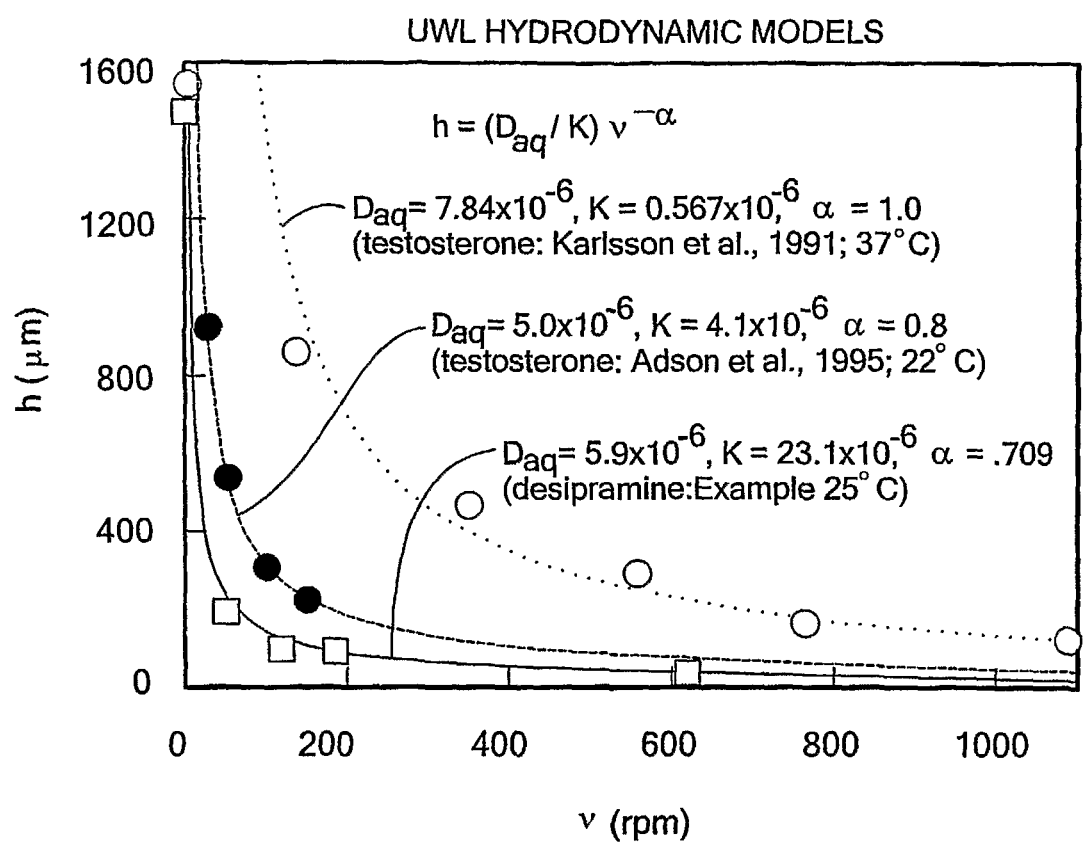
FIG. 15 shows a plot of the relationship between the thickness of aqueous boundary layers and v based on both literature studies and a device of the invention.

FIG. 15 shows the relationship between h and v, comparing the results from literature to those of this example using a device of the invention. As shown, the solid circles are based on testosterone data at 22° C. from Adson et al., J. Pharm. Sci., 84, pp. 1197-1204 (1995). The dashed line was calculated from the equation $$h = \left(\frac{D_{aq}}{K}\right)v^\alpha$$

using $D_{aq}$ at a value of $5.0 \times 10^{-6}$ cm s$^{-1}$, K being $4.1 \times 10^{-6}$ cm s$^{-1}$ and $\alpha$ at 0.8. The open circles represent testosterone at 37° C. from data taken by Karlsson et al., Int. J. Pharm., 7, pp. 55-64 (1991). The dotted curve in FIG. 15 is based on $D_{aq}$ at a value of $7.84 \times 10^{-6}$ cm s$^{-1}$, K equal to $0.57 \times 10^{-6}$ cm s$^{-1}$ and $\alpha$ at 1. In view of the higher K value in the work of Adson et al., J. Pharm. Sci., 84, pp. 1197-1204 (1995), it appears that permeation from the donor plate with support comprising Caco-2 type cells to new and fresh acceptor plates every five minutes, which is generally referred to as the "break" sandwich procedure, yields a more efficient mixing model.

The efficiency of break sandwich procedures can often produce an efficient mixing model as a rigorous sink state can be readily maintained so that the back flux of the molecular entity may be substantially eliminated. In addition, only the resistance of the boundary layer along the donor side of the permeation barrier can contribute to the kinetics related to mass transport. As a result, the solid circle boundary layer thicknesses are less than half of those of the open circles for any given stirring speed. The data for desipramine based on a PAMPA using a device of the invention are indicated by the square points fitted to a solid line curve with $D_{aq}$ having a value of $5.9 \times 10^{-6}$ cm s$^{-1}$, K being $23 \times 10^{-6}$ cm s$^{-1}$ and $\alpha$ at 0.71. As is evident from FIG. 15, the stirring efficiency using a device of the invention is significantly better than that reported in the literature.

While the present invention has been described herein in conjunction with a preferred embodiment, a person of ordinary skill in the art, after reading the foregoing specification, will be able to effect changes, substitutions of equivalents and other alterations to the devices and methods that are set forth herein. Each embodiment described above can also have included or incorporated therewith such variations as disclosed with regard to any or all of the other embodiments. For example, an insert well or receiving vessel can include any type of stirring member that has been described above or any of those known in the art that are suitable for solution agitation. Similarly, for example, constrictions, retaining members or retaining means or a combination thereof can be included with any one of the embodiments described herein. It is therefore intended that protection granted by Letter Patent hereon be limited in breadth only by the definitions that are contained in the appended claims and any equivalents thereof.

What is claimed is:

1. A permeation device for reducing boundary layer thickness, the device comprising:
    a receiving vessel, wherein the receiving vessel comprises an aperture;
    an insert well partially disposed in the aperture of the receiving vessel, the insert well having a lower section, wherein the lower section of the insert well comprises a porous support; and
    a magnetic stirring member rotatable about a horizontal axis, wherein the stirring member is disposed in the insert well; wherein the insert well includes a constriction about the interior of the insert well for engaging an outer portion of the stirring member at rest and as it rotates about a horizontal axis and preventing the stirring member from making physical contact with the porous support.

2. The device of claim 1, wherein the porous support comprises a biological material.

3. The device of claim 1, wherein the porous support comprises a biomimetic material.

4. The device of claim 1, wherein the porous support is adapted for a molecular entity to permeate therethrough.

5. The device of claim 4, wherein the molecular entity permeates from a solution, the solution disposed in the receiving vessel or insert well.

6. The device of claim 4, wherein a portion of the solution adjacent to the porous support comprises a boundary layer.

7. The device of claim 6, wherein the boundary layer has at least one thickness.

8. The device of claim 6, wherein the stirring member disposed in the insert well agitates the solution.

9. The device of claim 8, wherein agitating the solution changes the thickness of the boundary layer.

10. The device of claim 9, wherein controllably agitating the solution adjustably changes the thickness of the boundary layer.

11. The device of claim 8, wherein the thickness of the boundary layer is less than about 500 μm.

12. The device of claim 11, wherein the thickness of the boundary layer is less than about 100 μm.

13. The device of claim 12, wherein the thickness of the boundary layer is less than about 50 μm.

14. The device of claim 1, wherein the device further comprises a magnet positioned with respect to the insert well, the magnet operable for moving the stirring member.

15. The device of claim 14, wherein the magnet is connected to a motor, the motor adapted to rotate the magnet.

16. The device of claim 15, wherein the motor is controlled to adjust rotation of the magnet.

17. The device of claim 1, wherein the device further comprises a vibrational body positioned with respect to the receiving vessel, the vibrational body operable for moving the stirring member.

18. The device of claim 1, wherein the device further comprises a second stirring member, the second stirring member disposed in the receiving vessel.

19. The device of claim 1, wherein the constriction is ring-shaped.

20. The device of claim 19, wherein the stirring member is disk-shaped or donut-shaped and includes an outer diameter that is larger than an inside diameter of the ring-shaped constriction.

21. The device of claim 18, wherein the second stirring member comprises a molecular entity.

22. The device of claim 1, wherein the stirring member comprises a molecular entity.

23. The device of claim 1, wherein the device further comprises a material disposed in the receiving vessel.

24. The device of claim 23, wherein the material is a biological material, biomimetic material or a combination thereof.

25. The device of claim 1, wherein the device further comprises an acceptor plate, the acceptor plate comprising a plurality of receiving vessels or insert wells.

26. The device of claim 1, wherein the device further comprises a donor plate, the donor plate comprising a plurality of receiving vessels or insert wells.

27. A permeation device for reducing boundary layer thickness, the device comprising:
  a receiving vessel having an upper section, the upper section of the receiving vessel comprising a porous support, wherein the receiving vessel comprises an aperture;
  an insert well partially disposed in the aperture of the receiving vessel; and
  a magnetic stirring member rotatable about a horizontal axis, wherein the stirring member is disposed in the insert well;
  wherein the insert well includes a constriction about the interior of the insert well for engaging an outer portion of the stirring member at rest and as it rotates about a horizontal axis and preventing the stirring member from making physical contact with the porous support.

28. The device of claim 27, wherein the porous support comprises a biological material.

29. The device of claim 27, wherein the porous support comprises a biomimetic material.

30. The device of claim 27, wherein the porous support is adapted for a molecular entity to permeate therethrough.

31. The device of claim 30, wherein the molecular entity permeates from a solution, the solution disposed in the receiving vessel or insert well.

32. The device of claim 27, wherein the device further comprises a second stirring member, the second stirring member disposed in the receiving vessel.

33. A permeation device for monitoring concentrations of a molecular entity in a solution, the device comprising:
  a receiving vessel, wherein the receiving vessel comprises an aperture;
  an insert well partially disposed in the aperture of the receiving vessel, the insert well having a lower section, wherein the lower section of the insert well comprises a porous support;
  a solution, wherein the solution is disposed in the insert well;
  a magnetic stirring member rotatable about a horizontal axis and comprising a molecular entity, wherein the stirring member is disposed in the insert well, the stirring member adapted for dissolution of the molecular entity into the solution disposed in the insert well; and
  a probe disposed in the aperture of the receiving vessel, the probe capable of monitoring concentrations of the molecular entity in the solution;
  wherein the insert well includes a constriction about the interior of the insert well for engaging an outer portion of the stirring member at rest and as it rotates about a horizontal axis and preventing the stirring member from making physical contact with the porous support.

34. A method for reducing boundary layer thickness, the method comprising:
  providing a permeation device comprising
    a receiving vessel comprising an aperture,
    an insert well partially disposed in the aperture of the receiving vessel,
    a porous support, wherein the porous support is disposed in a lower section of the insert well or an upper section of the receiving vessel, and
    a magnetic stirring member rotatable about a horizontal axis, the stirring member disposed in the insert well;
  wherein the insert well includes a constriction about the interior of the insert well for engaging an outer portion of the stirring member at rest and as it rotates about a horizontal axis and preventing the stirring member from making physical contact with the porous support;
  permeating a molecular entity through the porous support, the molecular entity permeating from a solution disposed in the insert well, wherein a portion of the solution adjacent to the porous support comprises a boundary layer;
  moving the stirring member for agitation of the solution by supporting the stirring member with the constriction and rotating it about a horizontal axis while restraining it from physical contact with the porous support; and
  changing a thickness of the boundary layer by agitation of the solution.

35. The method of claim 34, wherein the porous support comprises a biological material.

36. The method of claim 34, wherein the porous support comprises a biomimetic material.

37. The method of claim 34, wherein agitation of the solution adjustably changes the thickness of the boundary layer.

38. The method of claim 37, wherein a magnet positioned with respect to the insert well moves the stirring member.

39. The method of claim 37, wherein a vibrational body positioned with respect to the insert well moves the stirring member.

40. The method of claim 34, wherein the thickness of the boundary layer is less than about 500 µm.

41. The method of claim 40, wherein the thickness of the boundary layer is less than about 100 µm.

42. The method of claim 41, wherein the thickness of the boundary layer is less than about 50 µm.

43. The method of claim 34, wherein the permeation device further comprises an acceptor plate, the acceptor plate comprising a plurality of receiving vessels or insert wells.

44. The method of claim 34, wherein the permeation device further comprises a donor plate, the donor plate comprising a plurality of receiving vessels or insert wells.

45. The device of claim 1 further comprising a controller device that regulates rotational speed of the stirring member, the device calibrated to produce known boundary layer thickness in the range from about 500 µm to about 15 µm at the interface between the porous support and a solution in the receiving vessel and/or a solution in the insert well.

46. The device of claim 1, wherein the magnetic stirring member has the form of a disc or donut.

47. The device of claim 27 further comprising a controller device that regulates rotational speed of the stirring member, the device calibrated to produce known boundary layer thickness in the range from about 500 µm to about 15 µm at the interface between the porous support and a solution in the receiving vessel and/or a solution in the insert well.

48. The device of claim 27, wherein the magnetic stirring member has the form of a disc or donut.

49. The method of claim 34, wherein the device further comprises a controller device that regulates rotational speed of the stirring member, the device calibrated to produce known boundary layer thickness in the range from about 500 µm to about 15 µm at the interface between the porous support and a solution in the receiving vessel and/or a solution in the insert well.

50. The method of claim 49, further comprising the step of adjusting the controller device to provide a desired boundary layer thickness.

* * * * *